US011357391B2

(12) United States Patent
Nakao et al.

(10) Patent No.: US 11,357,391 B2
(45) Date of Patent: Jun. 14, 2022

(54) ENDOSCOPE AND OPERATION PORTION

(71) Applicant: OLYMPUS CORPORATION, Tokyo (JP)

(72) Inventors: Yosuke Nakao, Hino (JP); Yuta Sato, Hachioji (JP); Shuji Saikawa, Hachioji (JP); Kaoru Tsuruoka, Kawaski (JP)

(73) Assignee: OLYMPUS CORPORATION, Tokyo (JP)

( * ) Notice: Subject to any disclaimer, the term of this patent is extended or adjusted under 35 U.S.C. 154(b) by 304 days.

(21) Appl. No.: 16/722,381

(22) Filed: Dec. 20, 2019

(65) Prior Publication Data
US 2020/0121165 A1    Apr. 23, 2020

Related U.S. Application Data

(63) Continuation of application No. PCT/JP2018/015776, filed on Apr. 16, 2018.

(30) Foreign Application Priority Data

Jun. 30, 2017 (JP) .............................. JP2017-129046

(51) Int. Cl.
*A61B 1/005* (2006.01)
*A61M 25/01* (2006.01)

(52) U.S. Cl.
CPC .......... *A61B 1/0052* (2013.01); *A61B 1/0057* (2013.01); *A61M 25/0136* (2013.01)

(58) Field of Classification Search
CPC ............................. A61B 1/0052; A61B 1/0057
See application file for complete search history.

(56) References Cited

U.S. PATENT DOCUMENTS

2011/0295068 A1    12/2011  Petersen et al.
2013/0047757 A1*   2/2013   Okamoto ........... A61B 1/00066
                                                74/89.22
(Continued)

FOREIGN PATENT DOCUMENTS

EP    2689715 A1    1/2014
EP    3047786 A1    7/2016
(Continued)

OTHER PUBLICATIONS

International Search Report dated Jul. 17, 2018 issued in PCT/JP2018/015776.

*Primary Examiner* — Alexandra L Newton
*Assistant Examiner* — Rynae E Boler
(74) *Attorney, Agent, or Firm* — Scully, Scott, Murphy & Presser, P.C.

(57) ABSTRACT

An endoscope includes: a plurality of wires each having a distal end connected to a bending portion of an insertion portion and a proximal end extending into an operation portion; one or more tubular members provided on the operation portion and including a first part extending in a direction of a longitudinal axis of the insertion portion, a second part provided on a proximal end side of the first part and extending in a side direction to the longitudinal axis, and a bent part connecting the first part and the second part, any one of the plurality of wires being inserted into the one or more tubular members, the first part and the second part being fixed to the operation portion; and a stopper fixed in the operation portion and arranged to prevent movement of the bent part by abutting on an inside of bending of the bent part.

4 Claims, 14 Drawing Sheets

(56) References Cited

U.S. PATENT DOCUMENTS

| | | | |
|---|---|---|---|
| 2013/0102846 A1* | 4/2013 | Sjostrom | A61B 1/07 600/110 |
| 2013/0331652 A1 | 12/2013 | Okamoto | |
| 2014/0114124 A1* | 4/2014 | Dresher | A61B 1/05 600/103 |
| 2014/0246014 A1 | 9/2014 | Petersen et al. | |
| 2015/0301096 A1* | 10/2015 | Dresher | G01R 29/0814 324/613 |
| 2016/0058267 A1 | 3/2016 | Petersen et al. | |
| 2016/0227986 A1 | 8/2016 | Yasunaga et al. | |
| 2016/0309985 A1* | 10/2016 | Akui | A61M 25/0147 |

FOREIGN PATENT DOCUMENTS

| | | |
|---|---|---|
| EP | 3078318 A1 | 10/2016 |
| JP | H03-215240 A | 9/1991 |
| JP | 2012-511356 A | 5/2012 |
| WO | WO 2010/066789 A1 | 6/2010 |
| WO | WO 2013/114913 A1 | 8/2013 |
| WO | WO 2015/068468 A1 | 5/2015 |
| WO | WO 2015/174139 A1 | 11/2015 |
| WO | WO-2015174139 * | 11/2015 |

* cited by examiner

ENDOSCOPE AND OPERATION PORTION

CROSS REFERENCE TO RELATED APPLICATION

This application is a continuation application of PCT/JP2018/015776 filed on Apr. 16, 2018 and claims benefit of Japanese Application No. 2017-129046 filed in Japan on Jun. 30, 2017, the entire contents of which are incorporated herein by this reference.

BACKGROUND OF THE INVENTION

1. Field of the Invention

The present invention relates to an endoscope and an operation portion that bends a part of an insertion portion by pulling a wire.

2. Description of the Related Art

An endoscope having a form capable of bending a bending portion provided on an elongated insertion portion insertable into a living body, a machine, or the like is known. In International Publication No. WO2015/068468, for example, there is disclosed an endoscope capable of changing a bending direction of a bending portion and an angle of the bending by changing the pulling amount of a plurality of wires connected to the bending portion in accordance with a direction and an angle in which a joy stick lever provided on an operation portion is pushed down.

Further, in FIG. 28 of International Publication No. WO2015/068468, a technology using a pulley on which a wire is hooked in order to change a travelling direction of a wire inside the operation portion is disclosed.

SUMMARY OF THE INVENTION

An endoscope according to an aspect of the present invention includes: an insertion portion including a bending portion; a plurality of wires each having a distal end connected to the bending portion and inserted into the insertion portion; an operation portion fixed in a proximal end of the insertion portion, the plurality of wires extending in the operation portion from an inside of the insertion portion to an inside along a longitudinal axis of the insertion portion; a swinging mechanism provided on the operation portion and configured to swingably support an operation stick protruding from the operation portion, a pulling mechanism provided on the operation portion, proximal ends of the plurality of wires being connected to the pulling mechanism, the pulling mechanism being configured to change a pulling amount of each of the plurality of wires in accordance with an inclination angle and an inclination direction from a predetermined neutral position of the operation stick; one or more tubular members provided on the operation portion and including a first part extending in a direction of the longitudinal axis, a second part provided on a proximal end side of the first part and extending in a side direction to the longitudinal axis, and a bent part connecting the first part and the second part, any one of the plurality of wires being inserted into the one or more tubular members, the first part and the second part being fixed to the operation portion; and a stopper fixed in the operation portion and arranged so as to prevent movement of the bent part by abutting on an inside of bending of the bent part.

Further, an operation portion according to an aspect of the present invention includes at least one tubular member provided in an inside of the operation portion and including a first part in which the tubular member is fixed in the inside of the operation portion, a second part that extends in a direction different from the first part and is fixed, and a bent part in which the first part and the second part are bent and connected; and a stopper fixed in the inside of the operation portion and configured to prevent movement of the bent part by abutting on an inside of bending of the bent part.

DETAILED DESCRIPTION OF THE PREFERRED EMBODIMENTS

Figure 1:
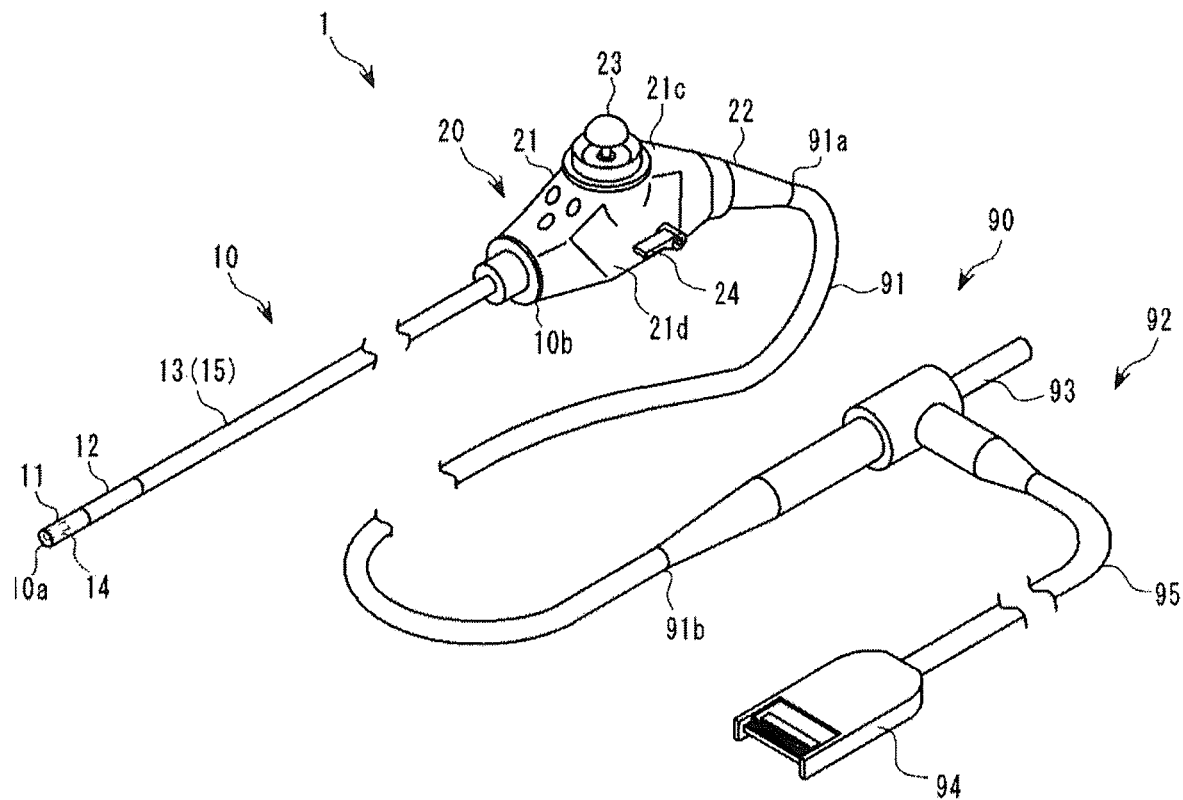
FIG. 1 is a diagram schematically showing a configuration of an endoscope according to a first embodiment.

Hereinafter, preferred embodiments of the present invention will be described with reference to the drawings. In each drawing used for the following description, the scale is different for each component in order to make each component large enough to be recognized in the drawing. The present invention is not limited only to the quantity of the component described in the figure, the shape of the component, the ratio of the size of the component, and the relative positional relationship of each component.

First Embodiment

FIG. 1 is a diagram schematically showing a configuration of an endoscope 1 according to the present embodiment. The endoscope 1 includes an insertion portion 10, which has an elongated shape, inserted into a subject, an operation portion 20 connected to a proximal end 10b of the insertion portion 10, and a universal cable 90 extended from the operation portion 20. Note that the subject into which the insertion portion 10 is inserted may be a living matter such as a person or a nonliving matter such as a machine or a building.

The insertion portion 10 includes a distal end portion 11, a bending portion 12, and a tubular portion 13, which are connected in this order, toward the proximal end 10b from a distal end 10a.

An image pickup apparatus 14 that picks up an image of an object such as an inside of a subject is arranged at the distal end portion 11. The image pickup apparatus 14 includes an objective lens and a solid-state imaging device such as a CCD or a CMOS image sensor. Further, an illuminating window (not shown) that emits light illuminating the object is provided on the distal end portion 11. Illumination light emitted by the illuminating window is emitted by a light source apparatus that is an external apparatus of the endoscope 1 and reaches the illuminating window through an optical fiber cable (not shown) inserted into the insertion portion 10. The image pickup apparatus 14 and the illuminating window in the endoscope are known, and therefore detailed descriptions are omitted.

The bending portion 12 bends in accordance with movement of an operation stick 23 provided on the operation portion 20. As will be described in detail later, a pulling mechanism 40 (not shown in FIG. 1) that pulls four wires connected to the bending portion 12 is provided on the operation portion 20. The pulling mechanism 40 causes the individual pulling amount of the four wires to be changed in accordance with a movement of the operation stick 23. A direction and angle of the bending are changed in accordance with a change in the pulling amount of the four wires in the bending portion 12. Note that a configuration of the bending portion 12 in which the direction and angle of the bending are changed in accordance with the change in the pulling amount of the four wires is similar to known technology, and therefore detailed descriptions are omitted.

The tubular portion 13 is a tubular portion for connecting a proximal end of the bending portion 12 and the operation portion 20 to be described later. The tubular portion 13 may have a rigid form such that the insertion portion 10 does not bend or a flexible form such that the insertion portion 10 bends along the subject into which the insertion portion 10 is inserted. An endoscope having an insertion portion a form of which is rigid is generally referred to as a rigid endoscope and an endoscope having an insertion portion a form of which is flexible is generally referred to as a flexible endoscope. In a medical field, for example, the rigid endoscope and the flexible endoscope are defined in ISO 8600-1:2015.

Figure 2:
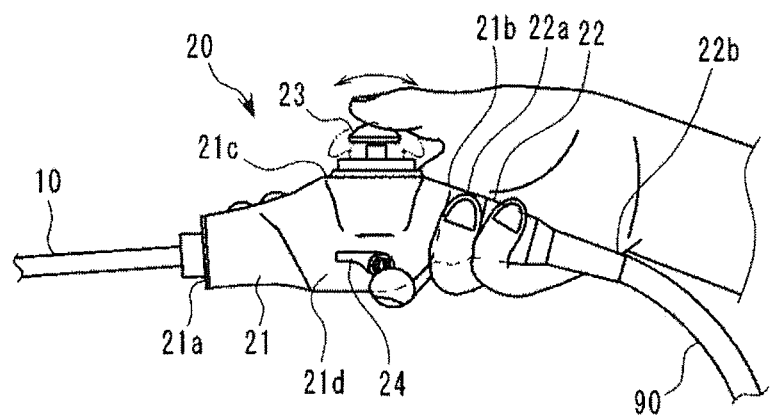
FIG. 2 is a diagram showing a state in which a grip of an operation portion is gripped by a right hand of a person.

The operation portion 20 includes a main body portion 21 to which the proximal end 10b of the insertion portion 10 is fixed and a grip 22 protruding from the main body portion 21. In FIG. 2, a state in which the grip 22 of the operation portion 20 is gripped by a right hand of a person is shown.

The main body portion 21 is made of an electrical insulating material such as resins in an outer surface. The insertion portion 10 is fixed to a distal end 21a of the main body portion 21 and the grip 22 is provided on a proximal end 21b on the opposite side to the distal end 21a of the main body portion 21. The insertion portion 10 and the grip 22 respectively extend in a substantially opposite direction from the main body portion 21.

The operation stick 23 protruding from the outer surface of the main body portion 21 is provided on the main body portion 21. The operation stick 23 is a swingable member around a predetermined supporting point P. A bending direction and angle of the bending portion 12 change in accordance with an inclination direction and an inclination angle from a neutral position of the operation stick 23. The neutral position of the operation stick 23 is a predetermined position in a swingable range of the operation stick 23, and in the present embodiment, the neutral position indicates a position in which a shape of the bending portion 12 is linear.

Further, as one example in the present embodiment, the operation stick 23 is arranged on a surface along a longitudinal direction of the insertion portion 10 in the outer surface of the main body portion 21. Further, a protruding direction from the main body portion 21 of the operation stick 23 in a case in which the operation stick 23 is placed in the neutral position is substantially orthogonal to the longitudinal direction of the insertion portion 10. Hereinafter, a surface on which the operation stick 23 of the main body portion 21 is provided is referred to as an upper surface.

A bending holding lever 24 is arranged on one of side surfaces intersecting the upper surface in the outer surface of the main body portion 21. Hereinafter, a surface on which the bending holding lever 24 of the main body portion 21 is provided is referred to as a left side surface 21d.

The bending holding lever 24 is an operating member for a user to operate a bending holding mechanism 70 to be described later. The bending holding lever 24 swings in a predetermined movable range around an axis substantially orthogonal to the left side surface 21d. In a case in which the bending holding lever 24 is placed at one end (free position) in the movable range, a resistance force for holding the operation stick 23 is small. Thus, when the user releases fingers from the operation stick 23, the operation stick 23 returns to a substantially neural position. On the other hand, in a case in which the bending holding lever 24 is placed at the other end (holding position) in the movable range, a resistance force in a case in which the operation stick 23 is caused to move increases, and therefore even if the user releases the fingers from the operation stick 23, a position of the operation stick 23 is held. Specifically, in a case in which the bending holding lever 24 is placed in the holding position, a shape of the bending portion 12 is fixed.

The grip 22 has a rod-like shape like a knife handle in an outer shape. As shown in FIG. 2, as one example in the present embodiment, the grip 22 can be gripped so as to be wrapped by a ring finger, a little finger, and a palm of the right hand of a person. In a case in which the grip 22 is gripped, an index finger is placed on the side of a distal end 22a of the grip 22 and the little finger is placed on the side of a proximal end 22b of the grip 22. Further, in a case in which the grip 22 is gripped, a thumb is placed along an upper surface of the main body portion 21 and a belly of the thumb can be touched with the operation stick 23.

As shown in FIG. 2, in a case in which the user grips the grip 22 by the right hand and the operation portion 20 is held in a posture in which an upper surface 21c on which the operation stick 23 is provided faces upward, the left side surface 21d faces toward a left hand side of the user. Accordingly, the left side surface 21d can be operated by a left hand of the user.

The main body portion 21 and the grip 22 are hollow and internal spaces of the main body portion 21 and the grip 22 communicate with an internal space of the tubular insertion portion 10.

The universal cable 90 extends from the proximal end 22b of the grip 22. The universal cable 90 includes a flexible tube portion 91 and a connector portion 92. The universal cable 90 is hollow and an internal space of the universal cable 90 communicates with an internal space of the operation portion 20.

The flexible tube portion 91 is an elongated tubular portion having flexibility and an electrical cable, an optical fiber cable, or the like is inserted into an inside. A distal end 91a of the flexible tube portion 91 is fixed in the proximal end 22b of the grip 22 of the operation portion 20. The connector portion 92 is arranged at a proximal end 91b of the flexible tube portion 91.

The connector portion 92 is a portion that connects an electrical cable, an optical fiber cable, or the like to the external apparatus of the endoscope 1. The connector portion 92 according to the present embodiment includes a light source connecting portion 93 and an electrical connecting portion 94.

The light source connecting portion 93 can be mounted on the light source apparatus that emits illumination light. A proximal end of the optical fiber cable is exposed to the light source connecting portion 93. As described above, the optical fiber cable is inserted into the operation portion 20 and the insertion portion 10. The light source connecting portion 93 is mounted on the light source apparatus, and thereby the illumination light emitted by the light source apparatus can be transmitted to the illuminating window provided on the distal end portion 11 of the insertion portion 10 through the optical fiber cable.

The electrical connecting portion 94 is a plug-shaped portion including a plurality of electrical contact point parts and can be mounted on a receptacle part provided on a video processor that is the external apparatus of the endoscope 1. The electrical connecting portion 94 is mounted on the video processor, and thereby the image pickup apparatus 14 and the video processor are electrically connected to each other through an electrical cable inserted into the endoscope 1.

As one example in the present embodiment, the light source connecting portion 93 and the electrical connecting portion 94 are separated from each other and both are connected through a connecting cable 95 having flexibility. Note that, for example, in a case in which the light source apparatus and the video processor are configured as the same instrument, the light source connecting portion 93 and the electrical connecting portion 94 may be integrally configured.

Figure 3:
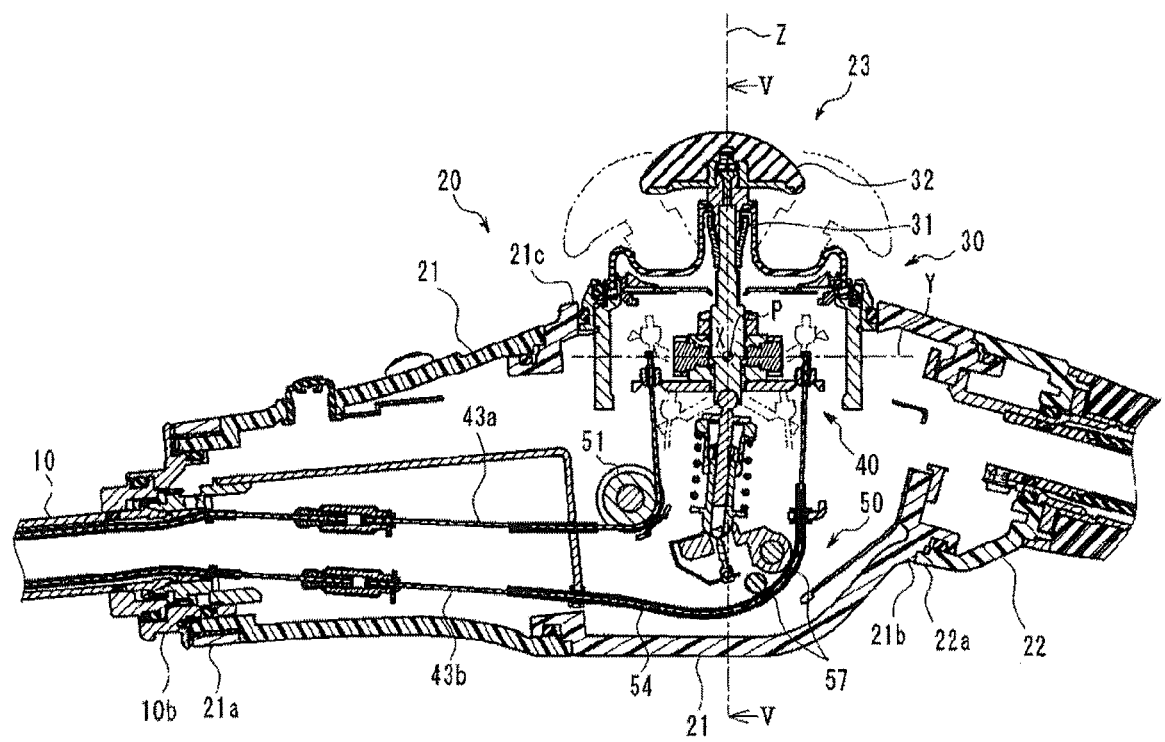
FIG. 3 is a cross-section view of the whole operation portion.
Figure 4:
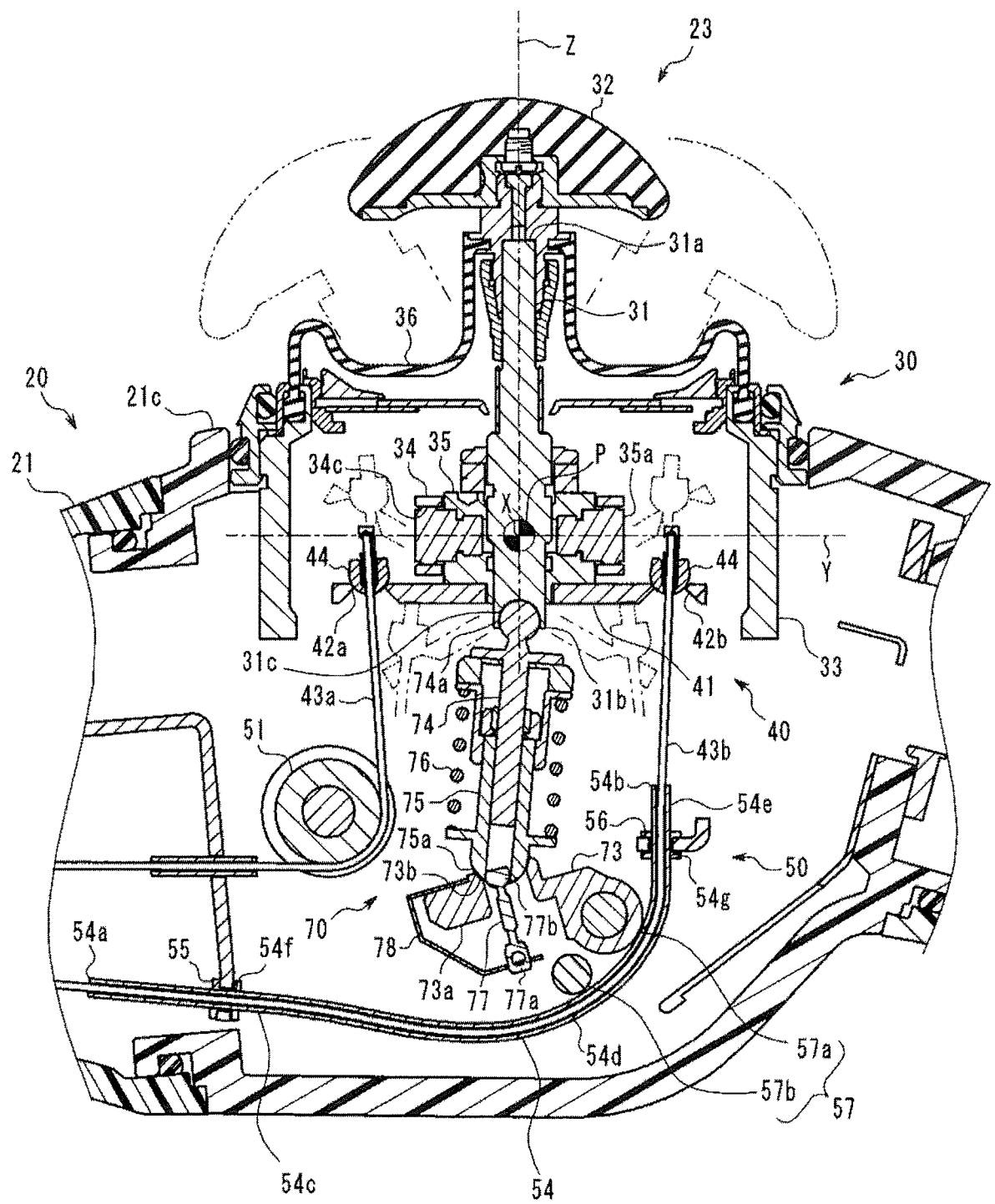
FIG. 4 is a partial enlarged view of FIG. 3.
Figure 5:
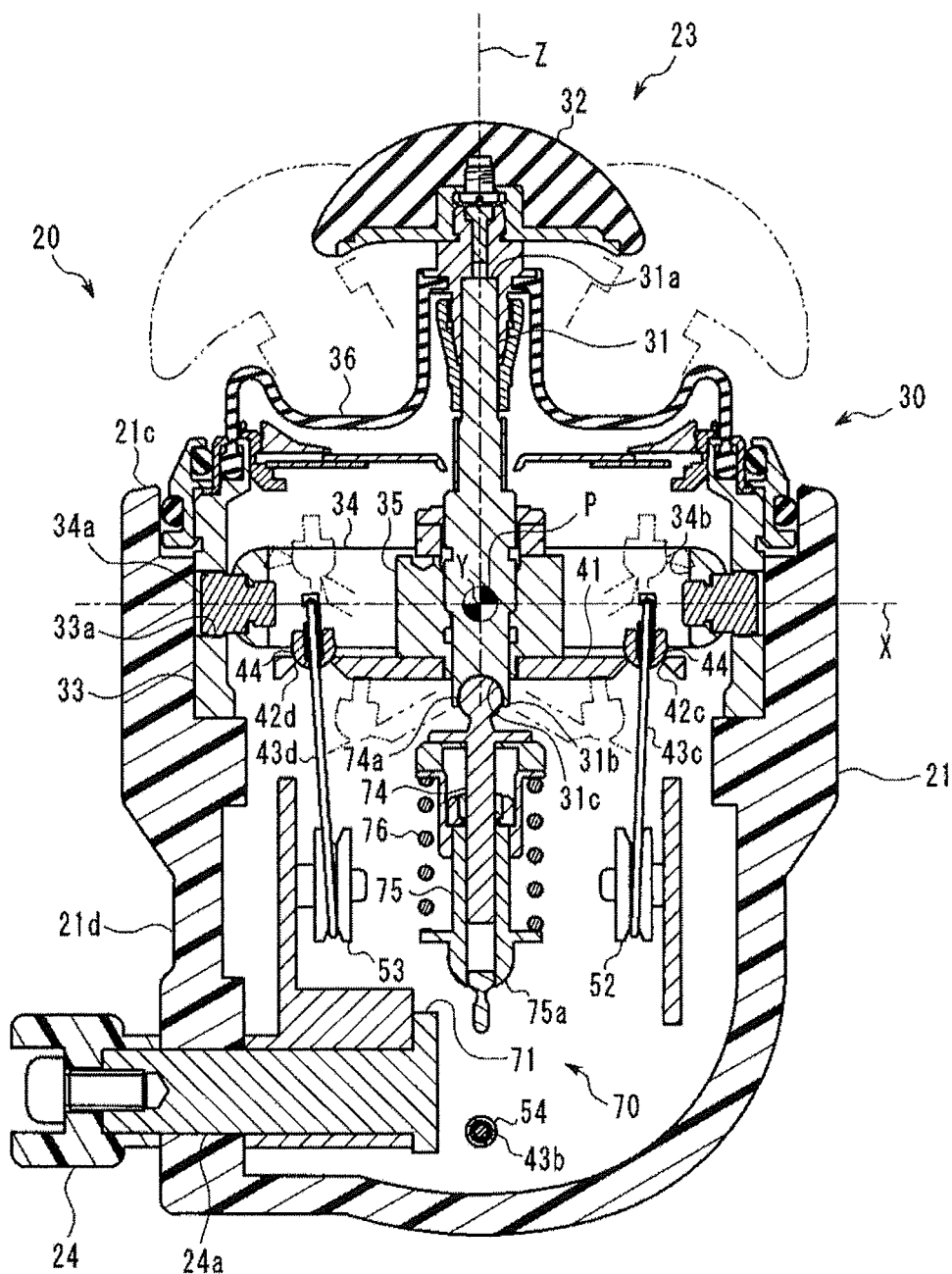
FIG. 5 is a V-V cross-section view of FIG. 3.

Next, a detailed configuration of the operation portion 20 will be described. FIG. 3 is a cross-section view of the whole operation portion 20. FIG. 4 is a partial enlarged view of FIG. 3. FIG. 5 is a V-V cross-section view of FIG. 3.

The operation stick 23 provided on the operation portion 20 includes a shaft 31 that swings around an X axis and a Y axis that are a pair of turning axes orthogonal to each other in the supporting point P. A knob 32 is fixed on an upper end part 31a that is a part protruding upward from the operation portion 20 of the shaft 31.

The X axis and the Y axis are linear axes positions of which are fixed to the main body portion 21 of the operation portion 20. Also, in a case in which the operation stick 23 is placed in the neutral position, the shaft 31 stands erectly to an X-Y plane. Specifically, in a case in which the operation stick 23 is placed in the neutral position, the shaft 31 is parallel to a Z axis orthogonal to the X axis and the Y axis. As one example in the present embodiment, the tubular portion 13 of the insertion portion 10 and the flexible tube portion 91 of the universal cable 90 extend in a direction along a Y-Z plane from a connecting part to the operation portion 20.

For purposes of explanation, hereinafter, regarding a direction along the Y axis, a direction toward the insertion portion 10 from the supporting point P is referred to as a front direction and a direction toward the universal cable 90 from the supporting point P is referred to as a rear direction. Further, regarding a direction along the Z axis, a direction in which the operation stick 23 protrudes from the operation portion 20 is referred to as an upward direction and an opposite direction thereto is referred to as a downward direction. Further, regarding a direction along the X axis, in a case in which the grip 22 is gripped by the right hand of the user as shown in FIG. 2, a direction in which a palm of the user is placed from the supporting point P is referred to as a right direction and an opposite direction thereto is referred to as a left direction.

Specifically, FIGS. 3 and 4 are diagrams in which a cross section of the operation portion 20 according to the Y-Z plane is viewed from the left direction and an upward direction in the diagram is an upward direction of the operation portion 20. Further, FIG. 5 is a diagram in which the cross section of the operation portion 20 according to an X-Z plane is viewed from the rear direction and an upward direction in the diagram is the upward direction of the operation portion 20.

Note that a name of a direction in the operation portion 20 is expedient and a posture of the operation portion 20 when the endoscope 1 is really used is not restricted.

Figure 6:
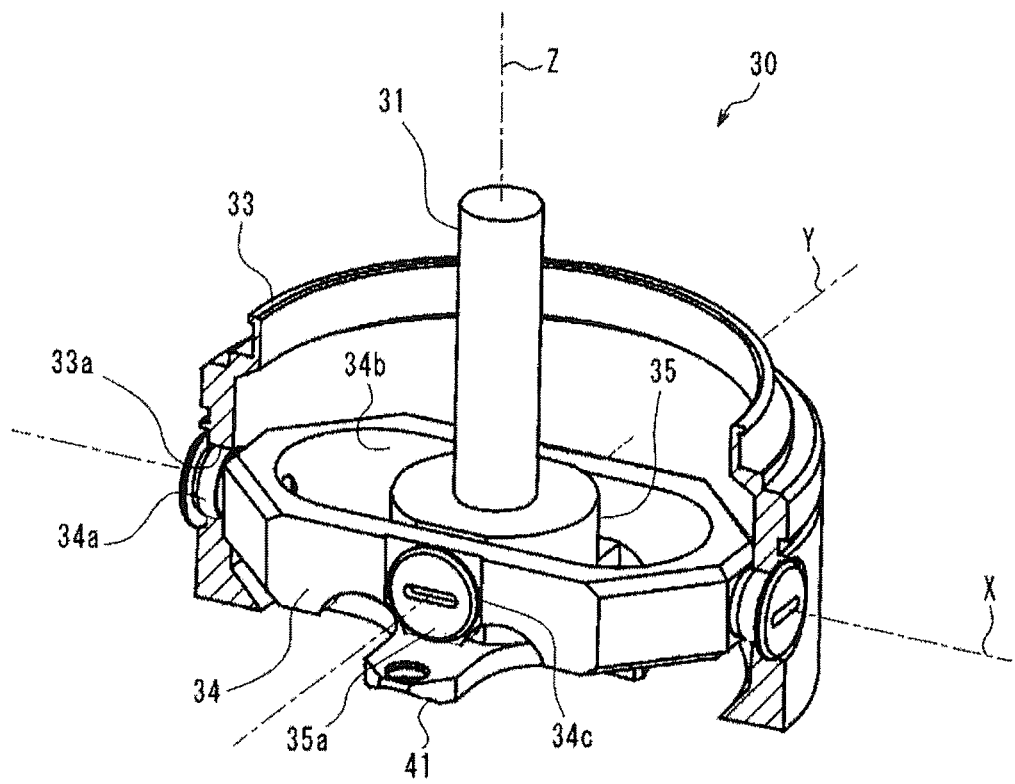
FIG. 6 is a diagram showing a schematic configuration of a swinging mechanism.

First, a configuration of a swinging mechanism 30 provided on the operation portion 20 will be described. In FIG. 6, a schematic configuration of the swinging mechanism 30 of the operation stick 23 is shown. As shown in FIG. 6, the swinging mechanism 30 includes a base 33, a first frame 34, and a second frame 35.

The base 33 is made of a substantially cylindrical member using the Z axis as a central axis. The base 33 is fixed on the main body portion 21 of the operation portion 20. An upper end part of the base 33 is opened in the upper surface 21c of the main body portion 21. The operation stick 23 protrudes above the upper surface 21c of the main body portion 21 through an upper opening of the base 33.

The first frame 34 is arranged on the inner side of the cylindrical base 33 and swings around the X axis toward the base 33. More specifically, a pair of first rotation axes 34a protruding in the right and left directions along the X axis from an outer circumference is provided on the first frame 34. The first rotation axis 34a is turnably supported around the X axis by a pair of bearings 33a provided in a site intersecting the X axis of the base 33.

A through-hole 34b centered on the supporting point P (intersection point of the X axis and the Y axis) is formed in the first frame 34. A cross-section shape of the through-hole 34b is an elongated oval shape in which a direction along the X axis is a longitudinal direction. In a case in which the operation stick 23 is placed in the neutral position, the through-hole 34b is opened in upward and downward directions.

The second frame 35 is arranged inside the through-hole 34b of the first frame 34 and swings around an axis orthogonal to the X axis in the supporting point P. More specifically, a pair of second rotation axes 35a protruding in both directions along a linear axis from an outer circumference is provided in the second frame 35. The second rotation axis 35a is turnably supported around an axis orthogonal to the X axis by a pair of bearings 34c provided on a site intersecting a linear axis orthogonal to the X axis in the supporting point P of the first frame 34.

The shaft 31 of the operation stick 23 is fixed in the second frame 35. The shaft 31 is arranged so that a central axis intersects the supporting point P. Through the above configuration, the shaft 31 swings around the X axis and the Y axis toward the base 33. A lower end part 31b of the shaft 31 protrudes below the supporting point P.

Next, a configuration of the pulling mechanism 40 provided on the operation portion 20 will be described. The pulling mechanism 40 causes the individual pulling amount of the four wires connected to the bending portion 12 to be changed in accordance with the movement of the operation stick 23.

As shown in FIGS. 4 and 5, the pulling mechanism 40 includes a flange portion 41 fixed in the shaft 31, and four wire engagement parts provided on the flange portion 41, the four wire engagement parts including a front engagement part 42a, a rear engagement part 42b, a right engagement part 42c, and a left engagement part 42d.

In the lower end part 31b of the shaft 31, the flange portion 41 protrudes in a direction substantially orthogonal to the shaft 31 from an outer circumference of the shaft 31. As shown in FIG. 6, in a case in which the shaft 31 swings around an axis orthogonal to the X axis toward the first frame 34, the flange portion 41 has a cross shape when viewed from an axial direction of the shaft 31 in order to avoid an interference with the first frame 34. Specifically, in a case in which viewed from a direction parallel to the Z axis when the operation stick 23 is placed in the neutral position, the flange portion 41 has a shape composed of four arm parts protruding from the shaft 31 to a front, rear, right, and left directions.

The front engagement part 42a, the rear engagement part 42b, the right engagement part 42c, and the left engagement part 42d provided on the flange portion 41 respectively are through-holes that penetrate the flange portion 41 in a direction substantially parallel to the shaft 31. In a case in which viewed from a direction parallel to the Z axis when the operation stick 23 is placed in the neutral position, the front engagement part 42a, the rear engagement part 42b, the right engagement part 42c, and the left engagement part 42d are arranged in the front, rear, right, and left directions from the shaft 31, respectively. Further, the front engagement part 42a, the rear engagement part 42b, the right engagement part 42c, and the left engagement part 42d respectively are arranged in a distance equivalent from the shaft 31.

A wire is inserted into each of the front engagement part 42a, the rear engagement part 42b, the right engagement part 42c, and the left engagement part 42d. Here, a wire inserted into the front engagement part 42a is referred to as a front wire 43a, a wire inserted into the rear engagement part 42b is referred to as a rear wire 43b, a wire inserted into the right engagement part 42c is referred to as a right wire 43c, and a wire inserted into the left engagement part 42d is referred to as a left wire 43d.

A wire stopper 44 is fixed on a site protruding above the flange portion 41 of each of the front wire 43a, the rear wire 43b, the right wire 43c, and the left wire 43d. The wire stopper 44 has an outer diameter larger than inner diameters of the front engagement part 42a, the rear engagement part 42b, the right engagement part 42c, and the left engagement part 42d that are through-holes into which individual wires are inserted.

Accordingly, the wire stopper 44 abuts on an upper surface of the flange portion 41, and thereby a relatively downward movement of the individual wires toward the flange portion 41 is restricted. Further, in the present embodiment, a tensile force is applied to the individual wires so that the wire stoppers 44 provided on the individual wires always abut on the upper surface of the flange portion 41.

In the pulling mechanism 40 configured as described above, the front engagement part 42a, the rear engagement part 42b, the right engagement part 42c, and the left engagement part 42d provided on the flange portion 41 respectively move upward or downward in accordance with the swinging around the supporting point P of the shaft 31 (operation stick 23). Therefore, a wire inserted into an engagement part that moves upward is pulled upward with the engagement part. The pulling amount (pulling distance) of the wire at this time is substantially proportional to an inclination angle from the neutral position of the shaft 31.

For example, in a case in which the upper end part 31a of the shaft 31 inclines so as to move forward from the neutral position, the rear engagement part 42b of the flange portion 41 moves upward, and therefore the rear wire 43b is pulled.

As described above, the pulling mechanism 40 has a configuration in which one end part of each of four wires 43a to 43d is pulled upward in the operation portion 20. Specifically, in the connecting part to the pulling mechanism 40, the four wires 43a to 43d substantially extend using the vertical direction as the longitudinal direction. On the other hand, the insertion portion 10 into which the four wires are inserted substantially extends forward from the operation portion 20 using the front-back direction as the longitudinal direction.

Accordingly, in the operation portion 20, the endoscope 1 according to the present embodiment includes a wire path changing portion 50 that bends a travelling path of the four wires 43a to 43d by approximately 90 degrees from the vertical direction to the front-back direction.

The wire path changing portion 50 includes three pulleys of a first pulley 51, a second pulley 52, a third pulley 53, and a coil pipe (tubular member) 54.

As shown in FIGS. 3 and 4, the first pulley 51 is arranged below the front engagement part 42a inside the operation portion 20. The first pulley 51 is rotatably supported around an axis parallel to the X axis. The front wire 43a extending downward from the front engagement part 42a is hooked on the first pulley 51. The front wire 43a extends downward from the front engagement part 42a, and afterward extends into the insertion portion 10 arranged before the operation portion 20 through the rear side and the lower side of the first pulley 51. As described above, the front wire 43a is connected to the bending portion 12 of the insertion portion 10.

As shown in FIG. 5, the second pulley 52 is arranged below the right engagement part 42c inside the operation portion 20. The second pulley 52 is rotatably supported around the axis parallel to the X axis. The right wire 43c extending downward from the right engagement part 42c is hooked on the second pulley 52. The right wire 43c extends downward from the right engagement part 42c, and afterward extends into the insertion portion 10 arranged before the operation portion 20 through the rear side and the lower side of the second pulley 52. As described above, the right wire 43c is connected to the bending portion 12 of the insertion portion 10.

Further, as shown in FIG. 5, the third pulley 53 is arranged below the left engagement part 42d inside the operation portion 20. The third pulley 53 is rotatably supported around the axis parallel to the X axis. The left wire 43d extending downward from the left engagement part 42d is hooked on the third pulley 53. The left wire 43d extends downward from the left engagement part 42d, and afterward extends into the insertion portion 10 arranged before the operation portion 20 through the rear side and the lower side of the third pulley 53. As described above, the left wire 43d is connected to the bending portion 12 of the insertion portion 10.

As described above, the wire path changing portion 50 according to the present embodiment bends a travelling path of the front wire 43a, the right wire 43c, and the left wire 43d by approximately 90 degrees by using three pulleys of the first pulley 51, the second pulley 52, and the third pulley 53.

As shown in FIG. 4, a coil pipe 54 is a tubular member into which the rear wire 43b is inserted, which is arranged inside the operation portion 20.

Hereinafter, regarding the coil pipe 54 into which the rear wire 43b is inserted, an end on the side connected to the bending portion 12 of the rear wire 43b is referred to as a distal end 54a, and an end on the side engaged on the rear engagement part 42b of the rear wire 43b is referred to as a proximal end 54b. The coil pipe 54 is arranged below the rear engagement part 42b.

In the longitudinal direction, the coil pipe 54 is composed of three sections of a first part 54c, a bent part 54d, and a second part 54e from the distal end 54a to the proximal end 54b.

The first part 54c extends along a longitudinal axis of the insertion portion 10. Specifically, the first part 54c extends in a direction substantially along the Y axis. The first part 54c is arranged below the first pulley 51. The first part 54c is inserted into a cylindrical first bush 55 fixed in the operation portion 20, and thereby is held in the above-described position and posture inside the operation portion 20. Specifically, a through-hole of the first bush 55 is opened in the direction substantially along the Y axis. Further, the first bush 55 is arranged below the first pulley 51.

The second part Me extends in a side direction to the longitudinal axis of the insertion portion 10. Specifically, the second part Me extends in a direction substantially along the Z axis. The second part Me is arranged behind the Z axis and above the first part 54c. The second part 54e is inserted into a second bush 56 that is a cylindrical fixed part fixed in the operation portion 20, and thereby is held in the above-described position and posture inside the operation portion 20. Specifically, a through-hole of the second bush 56 is opened in a direction substantially along the Z axis. Further, the second bush 56 is arranged behind the Z axis and above the first bush 55.

The bent part 54d is a part bent that connects the first part 54c and the second part 54e that are different from each other in an extending direction.

The rear wire 43b extends downward from the rear engagement part 42b and afterwards enters into the coil pipe 54 from the proximal end 54b of the coil pipe 54. Further, the rear wire 43b extends into the insertion portion 10 arranged before the operation portion 20 from the distal end 54a of the coil pipe 54. As described above, the rear wire 43b is connected to the bending portion 12 of the insertion portion 10. Accordingly, the coil pipe 54 arranged in the above shape bends a travelling path of the rear wire 43b by approximately 90 degrees.

A stopper 57 is arranged inside the bending of the bent part 54d having a bent shape of the coil pipe 54. The stopper 57 is made of a member fixed in the operation portion 20 before and below the second bush 56 that is the above-described fixed part. The stopper 57 abuts on a surface inside the bending of the bent part 54d to thereby restrict movement of the coil pipe 54.

In a case in which the rear wire 43b is pulled by the pulling mechanism 40 and a tensile force is applied to the rear wire 43b, the coil pipe 54 into which the rear wire 43b is inserted is deformed so that the bent part 54d moves in an inside direction of the bending and a curvature radius of the bending in a portion each held by the first bush 55 and the second bush 56 is made small.

Here, in the present embodiment, the movement of the bent part 54d of the coil pipe 54 is restricted by the stopper 57. Therefore, the curvature radius of the bending of the coil pipe 54 does not become smaller than a value determined by a positional relationship among three points in which the first bush 55, the second bush 56, and the stopper 57 are contacted with the coil pipe 54.

Generally, extremely small curvature radii of the coil pipe 54 and the rear wire 43b may cause an increase in a sliding resistance between the coil pipe 54 and the rear wire 43b or generation of kinks in the coil pipe 54 or the rear wire 43b. However, as described above, in the present embodiment, the curvature radius of the bent part 54d of the coil pipe 54 is prevented from getting extremely smaller by the stopper 57. Therefore, the stopper 57 can prevent the increase in the sliding resistance of the rear wire 43b or the generation of kinks in the coil pipe 54 or the rear wire 43b.

As described above, in the endoscope 1 according to the present embodiment, the travelling direction of the rear wire 43b can be changed in the operation portion 20 without using pulleys and without increasing a resistance force generated when pulling the rear wire 43b. The rear wire 43b is a wire arranged in the most downward direction inside the operation portion 20 among a plurality of wires included in the endoscope 1. Therefore, in the endoscope 1 according to the present embodiment, pulleys are not used for a mechanism that changes the travelling direction of the rear wire 43b to thereby make a size in a vertical direction of the operation portion 20 small. As shown in FIG. 2, the operation portion 20 is a portion gripped by the user. Therefore, when the operation portion 20 is miniaturized in the vertical direction, a freedom degree of a thumb touched with the operation stick 23 is increased and an operational feeling is improved.

More concretely, the stopper 57 according to the present embodiment includes two contact parts 57a and 57b. The two contact parts 57a and 57b are separated from each other in a cross section on the Y-Z plane shown in FIG. 4. Specifically, the two contact parts 57a and 57b are separated from each other in a direction parallel to a longitudinal direction of the coil pipe 54.

Note that the two contact parts 57a and 57b may be formed in the same member or may be formed in two different members, respectively. Also, shapes of the two contact parts 57a and 57b are not particularly limited.

As one example in the present embodiment, the two contact parts 57a and 57b have outer surfaces of two columnar members that are fixed independently to the operation portion 20 respectively. Further, central axes of the two columnar members are parallel to the X axis. Specifically, the two contact parts 57a and 57b according to the present embodiment each have a columnar surface the central axis of which is parallel to the X axis.

Accordingly, the stopper 57 according to the present embodiment abuts on a surface on the inside of the bending of the bent part 54d in two points of the two contact parts 57a and 57b. Accordingly, in the endoscope 1 according to the present embodiment, a tensile force is applied to the rear wire 43b and the bent part 54d of the coil pipe 54 moves in the inside direction of the bending. In this case, a flexure can be prevented from being generated in a site abutting on the stopper 57 of the coil pipe 54. The flexure of the coil pipe 54 is prevented from being generated, and thereby the sliding resistance between the coil pipe 57 and the rear wire 43b can be prevented from being increased.

Note that in a case in which a tensile force is not applied to the rear wire 43b, the two contact parts 57a and 57b are preferably separated from the coil pipe 54, and in a case in which the tensile force applied to the rear wire 43b is maximized, the two contact parts 57a and 57b are preferably arranged in a position abutting on the coil pipe 54. The case in which the tensile force applied to the rear wire 43b is maximized is a case in which the pulling amount of the rear wire 43b by the pulling mechanism 40 is maximized; in other words, a case in which the operation stick 23 is inclined up to a position in which the knob 32 moves forward most.

Second Embodiment

Hereinafter, a second embodiment of the present invention will be described. In the following, only differences from the first embodiment will be described, and the same components as those in the first embodiment will be denoted by the same reference numerals, and descriptions thereof will be omitted as appropriate.

Figure 7:
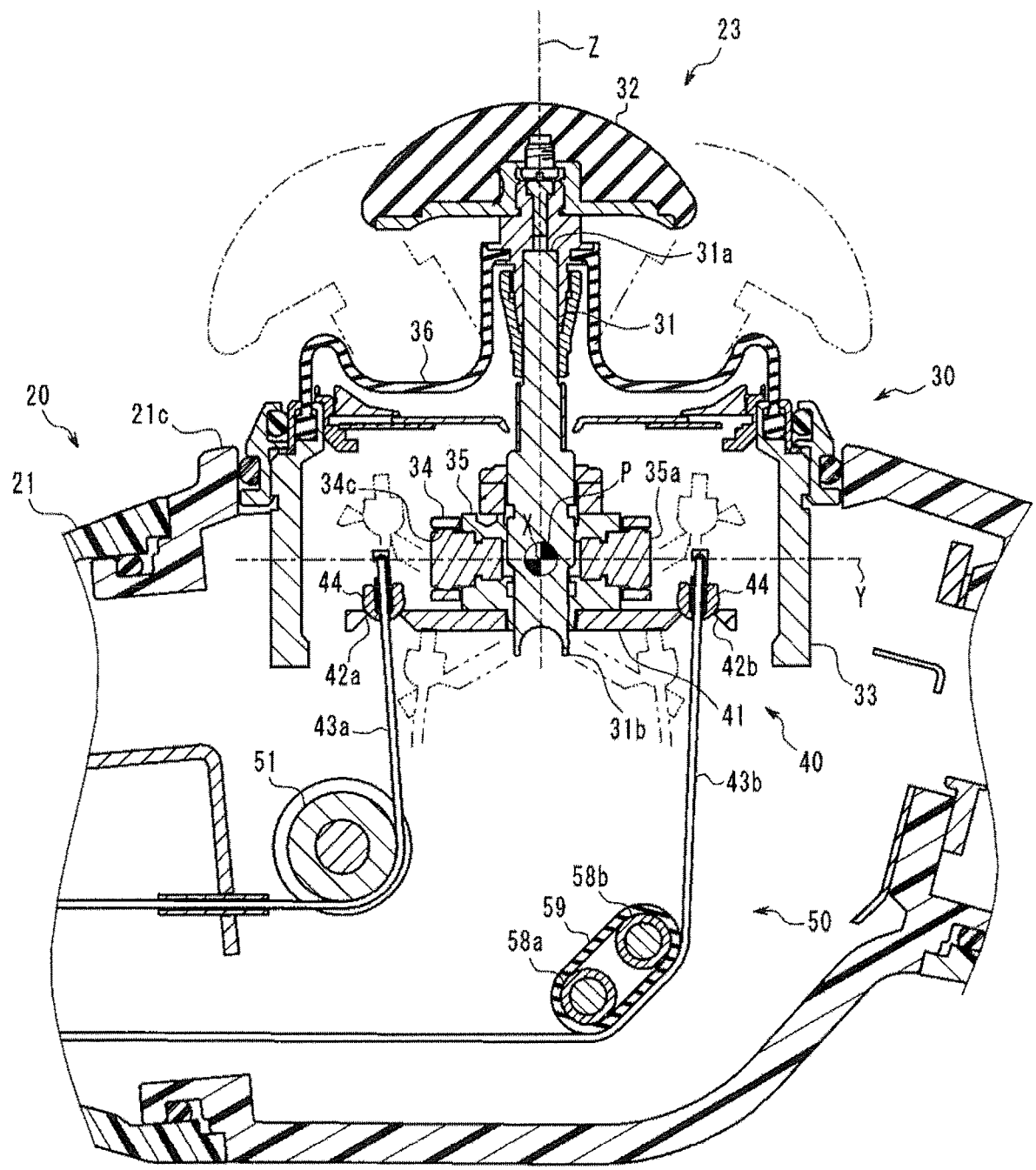
FIG. 7 is a cross-section view of an operation portion of an endoscope according to a second embodiment.

In FIG. 7, a cross-section view of the operation portion 20 of the endoscope 1 according to the present embodiment is shown. The endoscope 1 according to the present embodiment is different from the endoscope 1 according to the first embodiment in a configuration of the wire path changing portion 50.

The wire path changing portion 50 according to the present embodiment includes a pair of pulleys 58a and 58b arranged separately and a tubular belt 59 bridged across the pair of pulleys 58a and 58b. The pair of pulleys 58a and 58b is rotatably supported around the axis parallel to the X axis inside the operation portion 20. One pulley 58a is arranged before and below the other pulley 58b.

Further, the pulley 58b is arranged below the rear engagement part 42b of the pulling mechanism 40. The rear wire 43b extending below from the rear engagement part 42b is contacted with an outer circumference of the belt 59. The rear wire 43b expends below from the rear engagement part 42b and afterwards extends into the insertion portion 10 arranged before the operation portion 20 through the rear side and the lower side of the belt 59.

The belt 59 is contacted with the rear wire 43b, and therefore in a case in which the rear wire 43b moves in the longitudinal direction by the pulling mechanism 40, the belt 59 moves with the rear wire 43b. Accordingly, in the wire path changing portion 50 according to the present embodiment, the rear wire 43b does not slide over the belt 59, and therefore wear of the rear wire 43b can be prevented.

Further, in the wire path changing portion 50 according to the present embodiment, a part in which the rear wire 43b is bent is supported by the belt 59 bridged across the pair of pulleys 58a and 58b. Therefore, a force applied to individual pulleys can be made small and the wear of the pair of pulleys 58a and 58b can be suppressed.

Third Embodiment

Hereinafter, a third embodiment of the present invention will be described. In the following, only differences from the first embodiment will be described, and the same components as those in the first embodiment will be denoted by the same reference numerals, and descriptions thereof will be omitted as appropriate.

Figure 8:
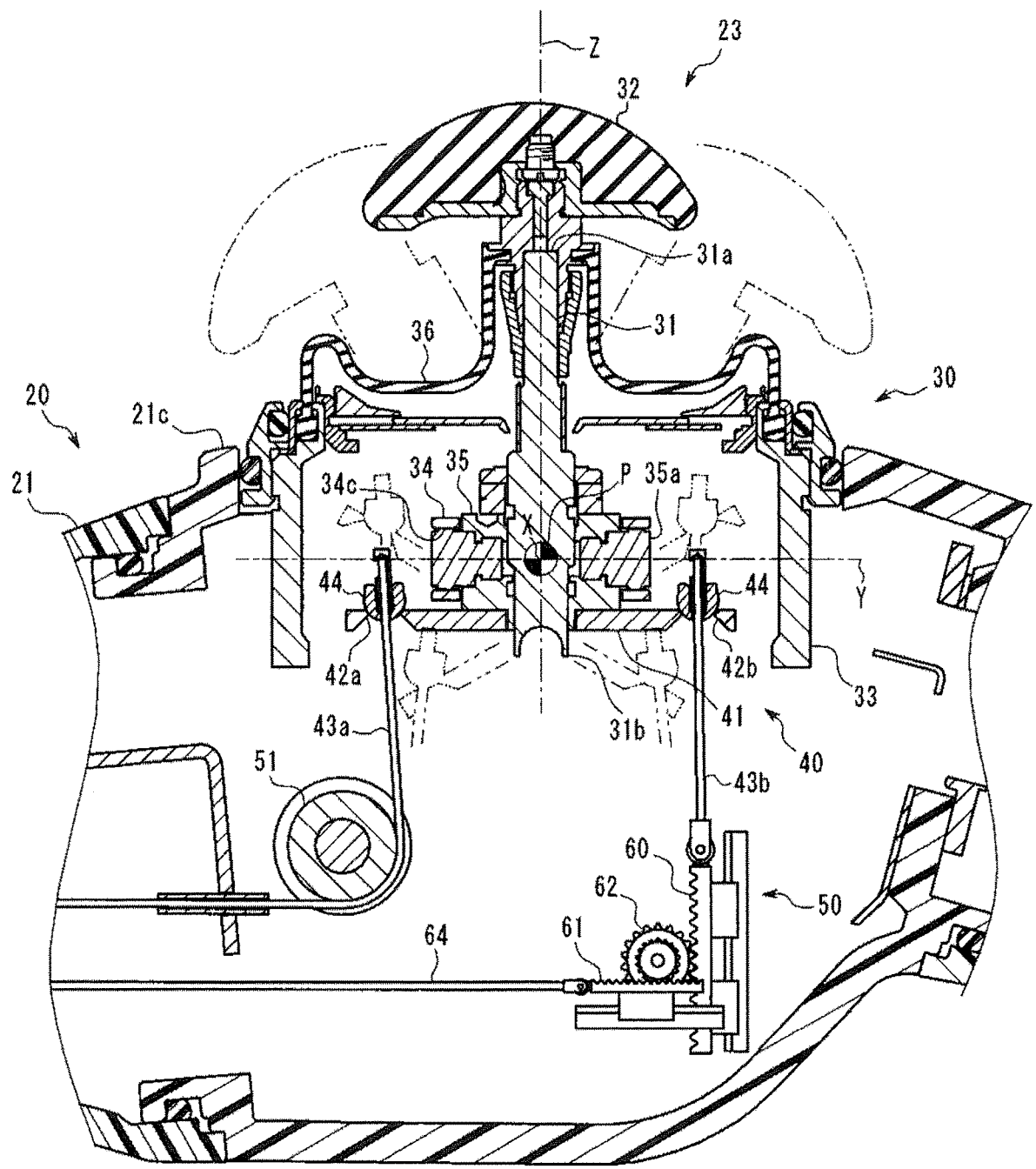
FIG. 8 is a cross-section view of an operation portion of an endoscope according to a third embodiment.

In FIG. 8, a cross-section view of the operation portion 20 of the endoscope 1 according to the present embodiment is shown. The endoscope 1 according to the present embodiment is different from the endoscope 1 according to the first embodiment in the configuration of the wire path changing portion 50.

The wire path changing portion 50 according to the present embodiment includes a first rack gear 60, a second rack gear 61, and a pinion gear 62.

The first rack gear 60 is arranged below the rear engagement part 42b of the pulling mechanism 40 and is supported by a linear bearing so as to slide in a direction substantially parallel to the Z axis. The pinion gear 62 rotatably supported around the axis parallel to the X axis engages with the first rack gear 60.

The second rack gear 61 is supported by the linear bearing so as to slide in a direction substantially parallel to the Y axis. Specifically, the sliding direction of the first rack gear 60 and the sliding direction of the second rack gear 61 are substantially orthogonal to each other. The pinion gear 62 also engages with the second rack gear 61. Accordingly, when the first rack gear 60 moves in the vertical direction, the second rack gear 61 moves in the front-back direction.

The rear wire 43b expending below from the rear engagement part 42b is connected to an upper end part of the first rack gear 60. Further, a proximal end of a connecting wire 64 a distal end of which is connected to the bending portion 12 of the insertion portion 10 is connected to a front end part of the second rack gear 61.

The wire path changing portion 50 according to the present embodiment converts a force direction in the vertical direction applied to the rear engagement part 42b by the pulling mechanism 40 to a force direction in the front-back direction and transmits the force to the connecting wire 64 without using pulleys.

In the endoscope 1 according to the present embodiment, a transmission direction of a force by a wire is converted without using a member slid by the wire such as a pulley. Therefore, a frictional resistance force or vibration generated when the wire slides is not generated.

Fourth Embodiment

Hereinafter, a fourth embodiment of the present invention will be described. In the following, only differences from the first embodiment will be described, and the same components as those in the first embodiment will be denoted by the same reference numerals, and descriptions thereof will be omitted as appropriate.

With reference to FIGS. 4, 5, 9, 10, and 11, a configuration of the bending holding mechanism 70 included in the endoscope 1 will be described.

In response to switching of a position of a bending holding lever 24 operated by the user, the bending holding mechanism 70 is switched to either a holding state in which a shape of the bending portion 12 is held or a free state in which a change in a shape of the bending portion 12 is allowed.

As described above, the bending holding lever 24 is provided so as to protrude to the left side surface 21d of the operation portion 20. The bending holding lever 24 swings around the axis parallel to the X axis against the operation portion 20. In a swinging range of the bending holding lever 24, one end is placed in a free position in which the bending holding mechanism 70 is in the free state and the other end is placed in a holding position in which the bending holding mechanism 70 is in the holding state.

Figure 9:
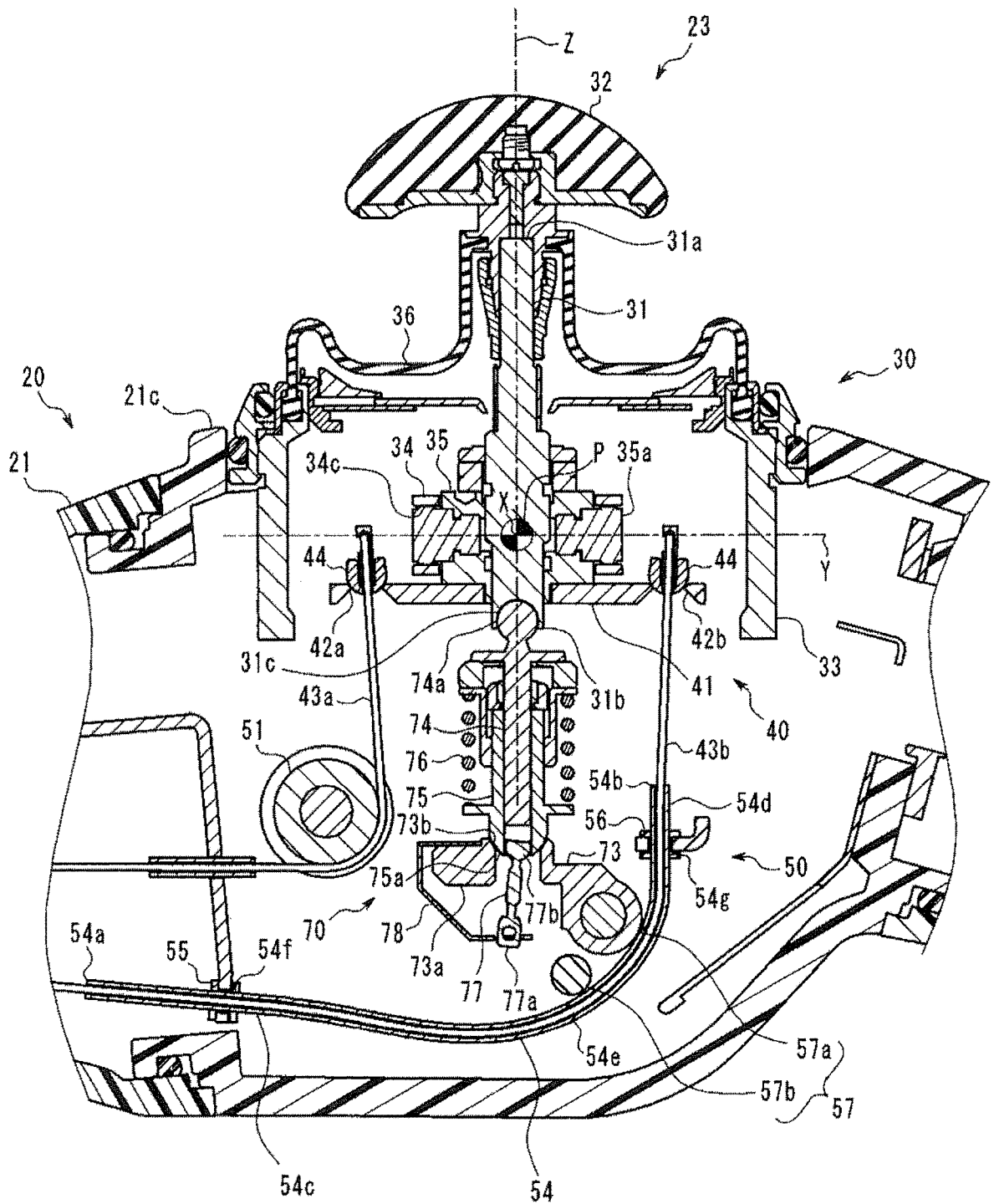
FIG. 9 is a diagram showing a case in which a bending holding lever is placed in a holding position in the same cross section as in FIG. 4 with respect to an operation portion according to a fourth embodiment.
Figure 10:
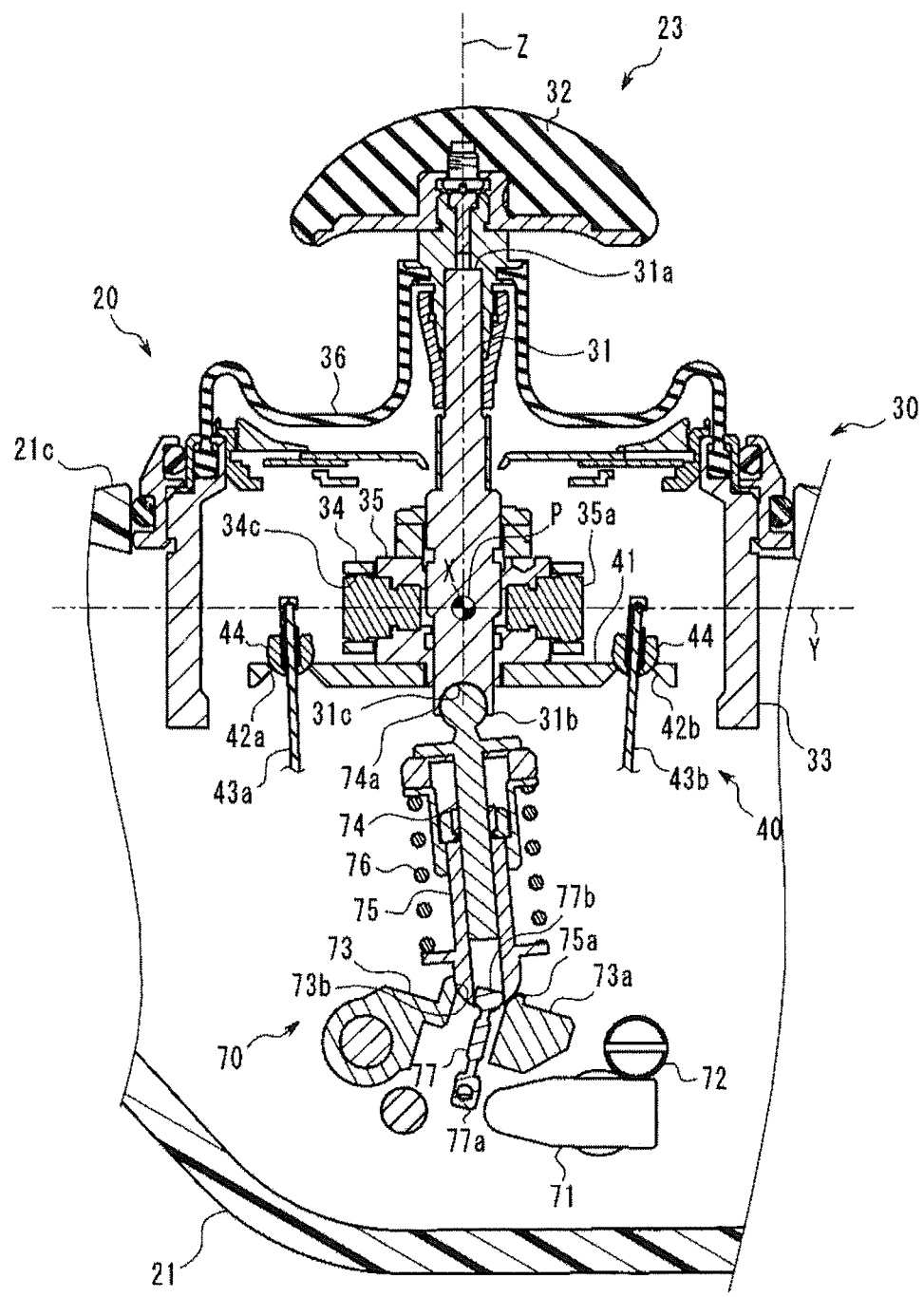
FIG. 10 is a diagram in which the cross section of the operation portion according to the fourth embodiment is viewed from an opposite side to FIG. 4.
Figure 11:
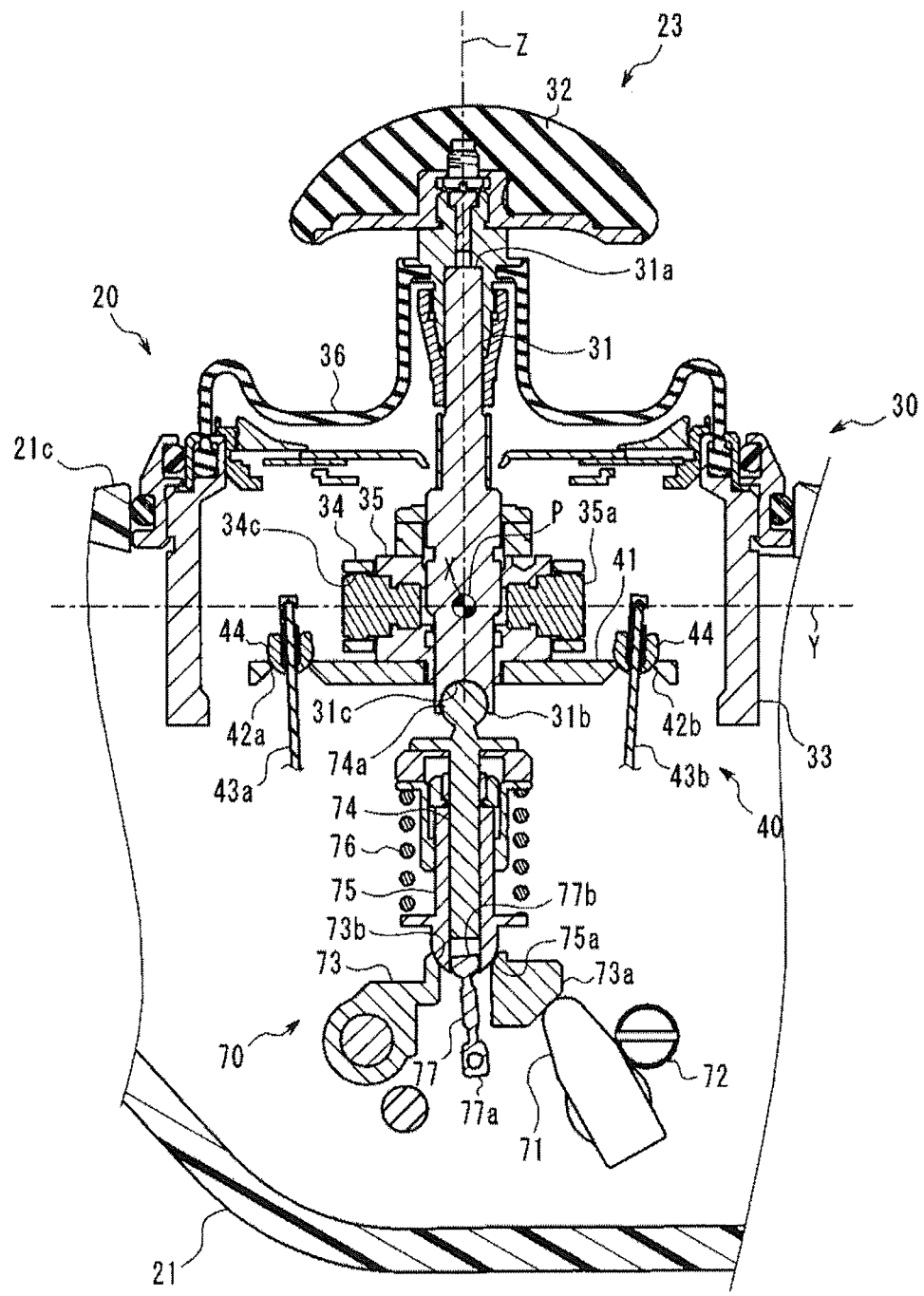
FIG. 11 is a diagram in which the cross section of the operation portion according to the fourth embodiment is viewed from an opposite side to FIG. 9.

FIGS. 4 and 5 show a case in which the bending holding lever 24 is placed in the free position. Further, in the same cross section as a cross section of FIG. 4, FIG. 9 shows a case in which the bending holding lever 24 is placed in the holding position. Further, FIGS. 10 and 11 are diagrams in which a cross section of the operation portion 20 according to the Y-Z plane is viewed from a right direction and an upward direction in the diagram is an upward direction of the operation portion 20. FIG. 10 shows a case in which the bending holding lever 24 is placed in the free position and FIG. 11 shows a case in which the bending holding lever 24 is placed in the holding position.

The bending holding mechanism 70 includes a cam 71, a cam stopper 72, a lever 73, a sliding axis 74, an outer cylinder 75, a compression coil spring 76, a retaining pin 77, and a plate spring 78.

The cam 71 is fixed in an end part protruding to the inside of the operation portion 20 in a swinging axis 24a of the bending holding lever 24. Specifically, the cam 71 swings around the swinging axis 24a parallel to the X axis with the bending holding lever 24.

As shown in FIGS. 10 and 11, in both ends in the swinging range, the cam 71 abuts on one columnar cam stopper 72 fixed on the inside of the operation portion 20. In the present embodiment, when viewed from a direction parallel to the X axis, the cam 71 has an elongated shape with a pair of extension parts, which is orthogonal to the swinging axis 24a, extending in a direction opposite to each other. In a case in which the bending holding lever 24 is placed in the free position, one extension part of the cam 71 abuts on the cam stopper 72. On the other hand, in a case in which the bending holding lever 24 is placed in the holding position, the other extension part of the cam 71 abuts on the cam stopper 72. As described above, in the endoscope according to the present embodiment, the operation portion 20 can be miniaturized because one cam stopper 72 is used in order to determine the swinging range of the bending holding lever 24.

In a case in which the bending holding lever 24 is placed in the free position, the elongated cam 71 has a posture in which the longitudinal direction is taken in the front-back direction. In a case in which the bending holding lever 24 is placed in the holding position, the cam 71 rises and falls so that the longitudinal direction is substantially taken along the vertical direction. The cam 71 that rises and falls pushes up the lever 73 to be described later.

The lever 73 is arranged adjacent to the cam 71 and swings around the axis parallel to the X axis against the operation portion 20. The lever 73 includes an arm part 73a extending to the cam 71 from the swinging axis. The arm part 73a of the lever 73 is arranged in a position intersecting the Z axis. Specifically, the arm part 73a is arranged below the supporting point P.

The above-described cam 71 is arranged below the arm part 73a, and in a case in which the bending holding lever 24 is placed in the free position, the cam 71 is separated from the arm part 73a. On the other hand, in a case in which the bending holding lever 24 is placed in the holding position, the cam 71 depresses the arm part 73a upward.

A bearing part 73b is formed at the arm part 73a of the lever 73. A lower end surface 75a of the outer cylinder 75 to be described later comes into slide contact with the bearing part 73b. Further, as shown in FIGS. 4 and 9, the plate spring 78 is fixed on the lever 73.

The sliding axis 74 is made of a rod-like member connected to the lower end part 31b of the shaft 31. A spherical part 74a is formed on an upper end part of the sliding axis 74. The spherical part 74a fits in a spherical bearing 31c formed on the lower end part 31b of the shaft 31. Specifically, the shaft 31 and the sliding axis 74 are connected through a so-called ball joint. An outer diameter of the spherical part 74a is slightly larger than an inner diameter of an opening in an entry of the spherical bearing 31c. Therefore, the spherical part 74a is prevented from slipping off from the spherical bearing 31c.

The outer cylinder 75 made of a cylindrical member slidably fits in an outer circumference on the lower end side of the sliding axis 74. The lower end surface 75a of the outer cylinder 75 is semispherical. The bearing part 73b of the lever 73 coming into slide contact with the lower end surface 75a of the outer cylinder 75 is a chamfered part of an end on the upper side of a circular through-hole penetrating through the arm part 73a.

The retaining pin 77 protrudes downward from the lower end surface 75a of the outer cylinder 75. An upper end part 77b of the retaining pin 77 is connected to a lower end of the outer cylinder 75 through a form of the ball joint. Specifically, the retaining pin 77 is prevented from slipping off from the lower end of the outer cylinder 75.

A lower end part 77a of the retaining pin 77 protrudes up to below the arm part 73a through the bearing part 73b penetrating through the arm part 73a of the lever 73. The lower end part 77a of the retaining pin 77 is connected to the plate spring 78 fixed on the arm part 73a of the lever 73. The plate spring 78 generates a force for energizing the retaining pin 77 downward.

An energizing force generated by the plate spring 78 is transmitted to the outer cylinder 75 via the retaining pin 77. Therefore, the bearing part 73b of the lever 73 and the lower end surface 75a of the outer cylinder 75 are always contacted with each other by the energizing force. As described above, in the endoscope 1 according to the present embodiment, the lower end surface 75a of the outer cylinder 75 is prevented from slipping off from the bearing part 73b of the lever 73 by using the retaining pin 77 and the plate spring 78. Accordingly, when the lever 73 swings, the outer cylinder 75 moves in the vertical direction with the arm part 73a.

The compression coil spring 76 is arranged on the outer circumferences of the sliding axis 74 and the outer cylinder 75 and generates a force for energizing the outer cylinder 75 relatively downward against the sliding axis 74.

In the bending holding mechanism 70 having the configuration described above, as shown in FIG. 10, in a case in which the bending holding lever 24 is placed in the free position, the cam 71 is separated from the arm part 73a. Therefore, the outer cylinder 75 and the arm part 73a move downward by the energizing force of the compression coil spring 76. In this case, the bending holding mechanism 70 does not apply a force to the shaft 31 connected to the sliding axis 74. Accordingly, in a case in which the bending holding lever 24 is placed in the free position, a resistance force for holding the shaft 31 (operation stick 23) is small and the user can move the shaft 31 freely.

On the other hand, as shown in FIG. 11, in a case in which the bending holding lever 24 is placed in the holding position, the arm part 73a of the lever 73 is fixed by the cam 71 in a position in which the arm part 73a of the lever 73 moves upward. In this case, the outer cylinder 75 moves upward and the compression coil spring 76 is compressed, and therefore the energizing force of the compression coil spring 76 is transmitted to the shaft 31 through the sliding axis 74. The sliding axis 74 and the shaft 31 are connected by the ball joint, and therefore the energizing force of the compression coil spring 76 is applied to the axial direction of the shaft 31. The resistance force for holding the shaft 31 (operation stick 23) is increased by the energizing force of the compression coil spring 76 input to the shaft 31. Therefore, even if the user releases fingers from the operation stick 23, a position of the operation stick 23 is held. Specifically, in a case in which the bending holding lever 24 is placed in the holding position, a shape of the bending portion 12 is fixed.

Figure 12:
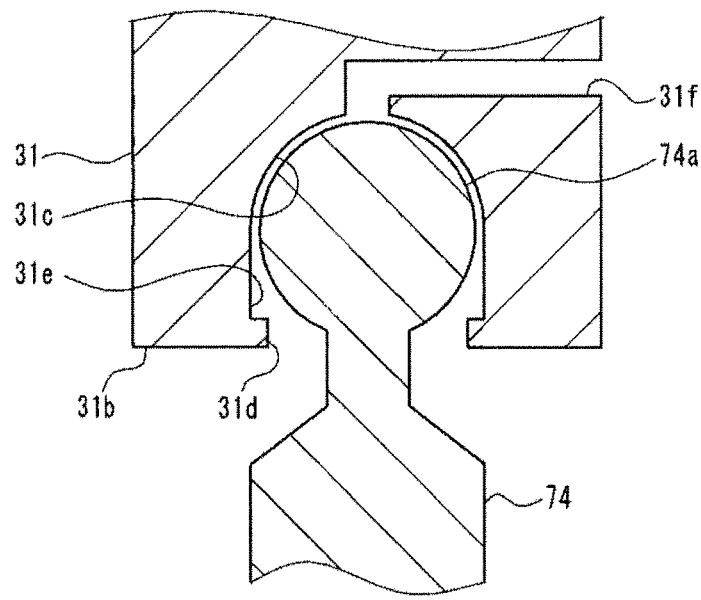
FIG. 12 is a diagram in which a cross section of a spherical bearing according to the fourth embodiment is enlarged.

FIG. 12 is a cross-section view in which the spherical bearing 31c formed in the lower end part 31b of the shaft 31 is enlarged.

As shown in FIG. 12, in an inner surface of the spherical bearing 31c according to the present embodiment, an enlarged diameter part 31e is formed in the vicinity of the opening 31d into which the spherical part 74a of the sliding axis 74 is press-fitted. The enlarged diameter part 31e is a part having an inner diameter larger than an outer diameter of the spherical part 74a.

In more detail, an upper part in the inner surface of the spherical bearing 31c in which the opening 31d is formed downward is semispherical and has a shape in slide contact with the spherical part 74a. On the other hand, when the spherical part 74a is energized relatively upward against the spherical bearing 31c, the enlarged diameter part 31e separated from the spherical part 74a is formed on a lower part of the inner surface.

When the spherical part 74a is press-fitted into the spherical bearing 31c, the vicinity of the opening 31d may be plastically deformed. When a plastically deformed part that is generated in the inner surface of the spherical bearing 31c depresses the spherical part 74a, an increase in the sliding resistance is caused between the spherical part 74a and the spherical bearing 31c. In the present embodiment, the enlarged diameter part 31e separated from the spherical part 74a is formed in the vicinity of the opening 31d, and thereby even if a plastic deformation is generated in the inner surface of the spherical bearing 31c, an increase in the sliding resistance can be prevented between the spherical part 74a and the spherical bearing 31c.

Further, in the present embodiment, an air hole 31f communicating with an outer circumferential surface of the shaft 31 is opened in the inner surface of the spherical bearing 31c. As in the present embodiment, the air hole 31f is provided in the inner surface of the spherical bearing 31c, and thereby when the spherical part 74a is press-fitted into the spherical bearing 31c, a space between the inside of the spherical bearing 31c and the spherical part 74a can be prevented from being made into an enclosed space by an influence of grease for sliding or the like, which can lead to reduction in a force necessary for press fitting and prevention of an increase in the sliding resistance due to the enclosed space.

Fifth Embodiment

Hereinafter, a fifth embodiment of the present invention will be described. In the following, only differences from the first embodiment will be described, and the same components as those in the first embodiment will be denoted by the same reference numerals, and descriptions thereof will be omitted as appropriate.

Figure 13:
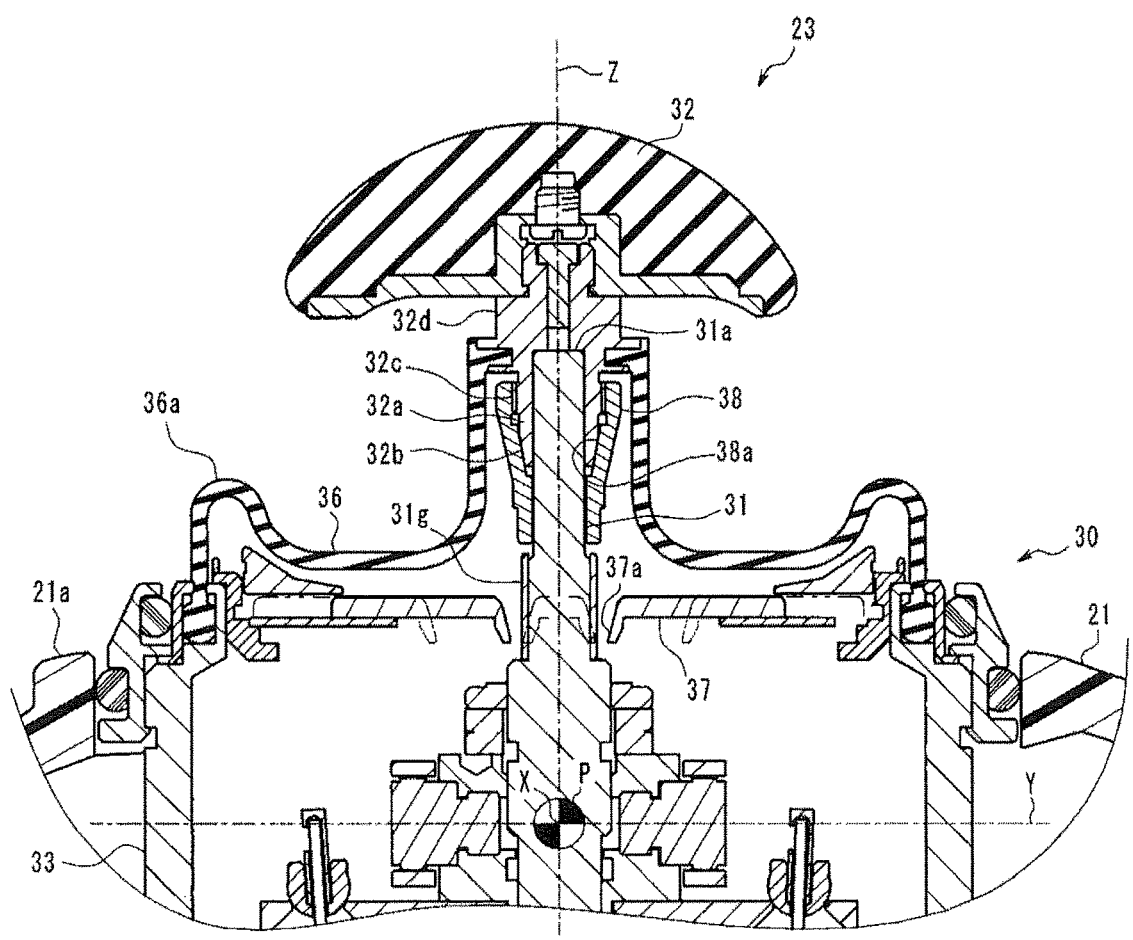
FIG. 13 is a diagram in which a cross section of an operation stick according to a fifth embodiment is enlarged.

FIG. 13 is a diagram in which a cross section of the operation stick 23 is enlarged. As described above, an upper end part of the base 33 of the swinging mechanism 30 is opened in the upper surface 21c of the main body portion 21. In the opening of the base 33, a rubber boot 36 is mounted in order to fill a gap generated between the opening and the operation stick 23. The rubber boot 36 is made of a film-like rubber member and an outer circumferential part of the rubber boot 36 is tightly contacted with the base 33. Further, an inner circumference of the through-hole provided in the central part of the rubber boot 36 is tightly contacted with an outer circumference of the operation stick 23. The rubber boot 36 is provided to thereby make the endoscope 1 into a waterproof structure.

Even if the operation stick 23 is reclined most from the neutral position, folds in bending 36a is provided so that the rubber boot 36 is not completely extended. The folds in bending 36a is provided on the rubber boot 36, and thereby a reaction force generated in a direction in which the rubber boot 36 is resistant to the movement of the operation stick 23 can be reduced.

Further, a circular plate 37 made of a circular-plate member parallel to the X-Y plane is arranged inside the rubber boot 36 in the opening of the base 33. A through-hole 37a into which the shaft 31 is inserted is formed in a central part of the circular plate 37. The circular plate 37 can move parallel to the X-Y plane along with the movement of the shaft 31 inserted into the through-hole 37a.

In a case a normal atmosphere inside the operation portion 20 is lower than a normal atmosphere outside the operation portion 20 by a change in an atmospheric pressure, or an implementation of cleansing or sterilization process of an autoclave etc., by providing the circular plate 37 inside the rubber boot 36, the rubber boot 36 is prevented from entering into the opening of the base 33. When the rubber boot 36 enters into the opening of the base 33, a damage such as scarring or break possibly occurs in the rubber boot 36. A force pushed to the inside is more applied to the rubber boot 36 when a normal atmosphere is changed inside the operation portion 20. Therefore, to prevent deformation, the circular plate 37 is preferably made of a material having high rigidity, such as a metal.

Here, in the present embodiment, a collar 31g made of a cylindrical member is arranged on a site contacted with the circular plate 37 around the shaft 31. The collar 31g is slidable in an axial direction and in a circumferential direction against the shaft 31. The collar 31g is provided on a site contacted with the circular plate 37 around the shaft 31, and thereby wear of the shaft 31 can be prevented, which is caused by contacting with or sliding on the circular plate 37.

Next, in the operation stick 23, a configuration in which the knob 32 is fixed in the shaft 31 will be described.

A spline working part that suppresses rotation of a cylindrical part 32a of the knob 32 to be described later is formed on an outer circumferential part of the upper end part 31a of the shaft 31.

The cylindrical part 32a that is cylindrical protrudes downward from a lower surface of the knob 32. The cylindrical part 32a fits in the upper end part 31a of the shaft 31.

A spline working part that engages with the spline working part of the upper end part 31a of the shaft 31 is formed on the inner circumferential surface of the cylindrical part 32a.

Although not shown in the figure, in the cylindrical part 32a, a slit (slot) is formed in an axial direction from a lower end. Further, a tapered surface 32b that gradually decreases in diameter toward the lower end and a male screw 32c that is formed above the tapered surface 32b are formed on the outer circumferential surface of the cylindrical part 32a.

A nut 38 is screwed to the male screw 32c. A tapered surface 38a that abuts on the tapered surface 32b is formed on the inner circumferential surface of the nut 38. The tapered surface 38a of the nut has a shape gradually decreasing in diameter toward the lower end.

The nut 38 is fastened to the male screw 32c of the cylindrical part 32a, and thereby an inner diameter of the cylindrical part 32a in which the slit is formed becomes small. Accordingly, when the nut 38 is fastened to the inside of the cylindrical part 32a in the state in which the upper end part 31a of the shaft 31 is inserted, the cylindrical part 32a is deformed so that the cylindrical part 32a fastens the shaft 31 inside, and therefore the cylindrical part 32a and the shaft 31 are fixed. Further, in the present embodiment, when an angle in which the spline working parts of the shaft 31 and the cylindrical part 32a engage with each other is changed, an angle of the knob 32 against the shaft 31 can be changed.

Further, in the present embodiment, a cross-section shape of a base portion 32d of the cylindrical part 32a is square or regular hexagonal. Therefore, by hooking a tool such as a wrench on the base portion 32d, a fastening work of the nut 38 can be performed without applying a force in a torsional direction to the shaft 31.

Further, in the present embodiment, a screw part such as the male screw 32c is configured so as not to be exposed to the outside of the endoscope 1. Therefore, a cleansing work of the endoscope 1 is facilitated.

Figure 14:
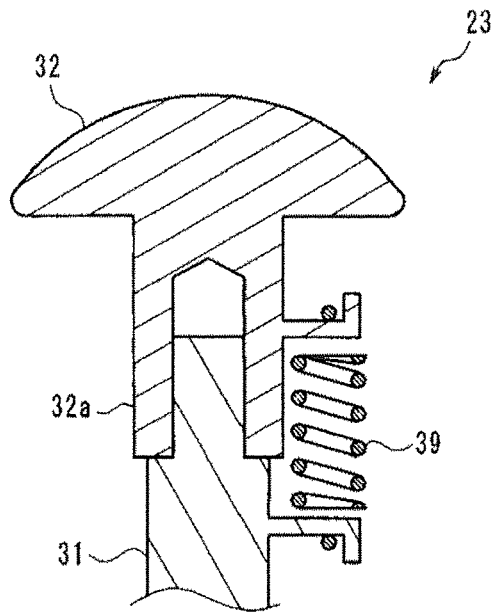
FIG. 14 is a diagram showing a modification of the operation stick according to the fifth embodiment.

Note that, in the present embodiment, fixing of the shaft 31 and the knob 32 is performed by fastening of the slot. However, a method for fixing the shaft 31 and the knob 32 is not limited to the present embodiment. As shown in FIG. 14 as a modification, for example, there may be used a configuration in which the shaft 31 and the knob 32 are combined, which fit into each other by using an axial member, and a cylindrical member, and slipping off of the fitting is prevented by an energizing force generated by a pulling coil spring 39 installed between both of the shaft 31 and the knob 32. Note that, in the modification, the pulling coil spring 39 may be arranged so as to be wound around an outer circumference of the shaft 31 or may be arranged in a hole formed inside the shaft 31.

Sixth Embodiment

Hereinafter, a sixth embodiment of the present invention will be described. In the following, only differences from the first embodiment will be described, and the same components as those in the first embodiment will be denoted by the same reference numerals, and descriptions thereof will be omitted as appropriate.

Figure 15:
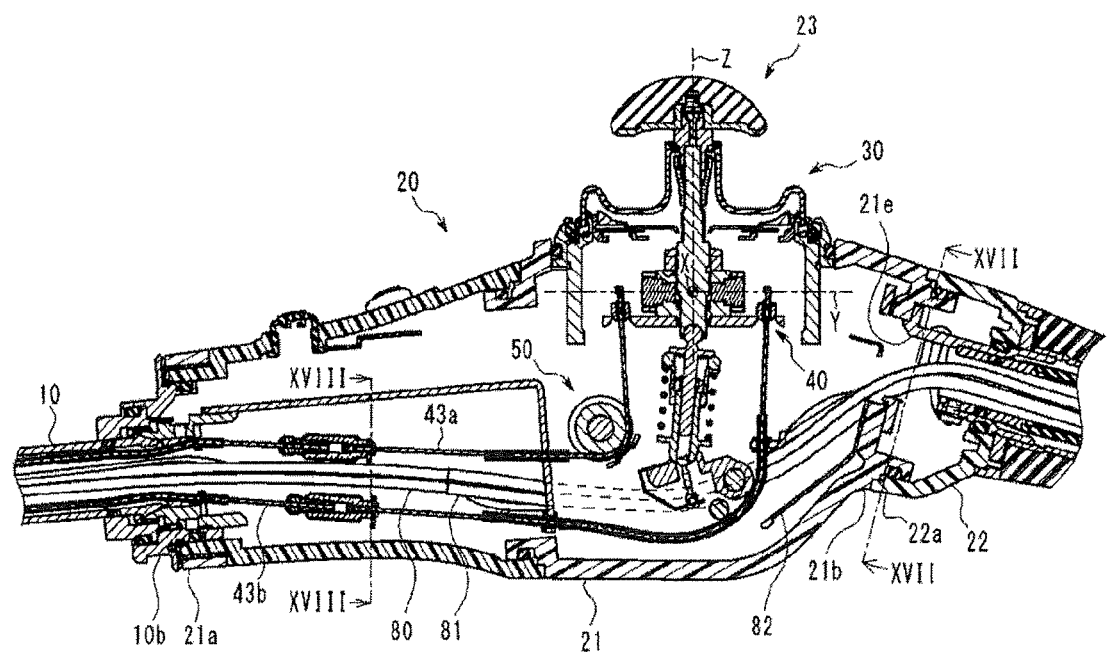
FIG. 15 is a cross-section view in which an inside of an operation portion according to a sixth embodiment is viewed from the left side.
Figure 16:
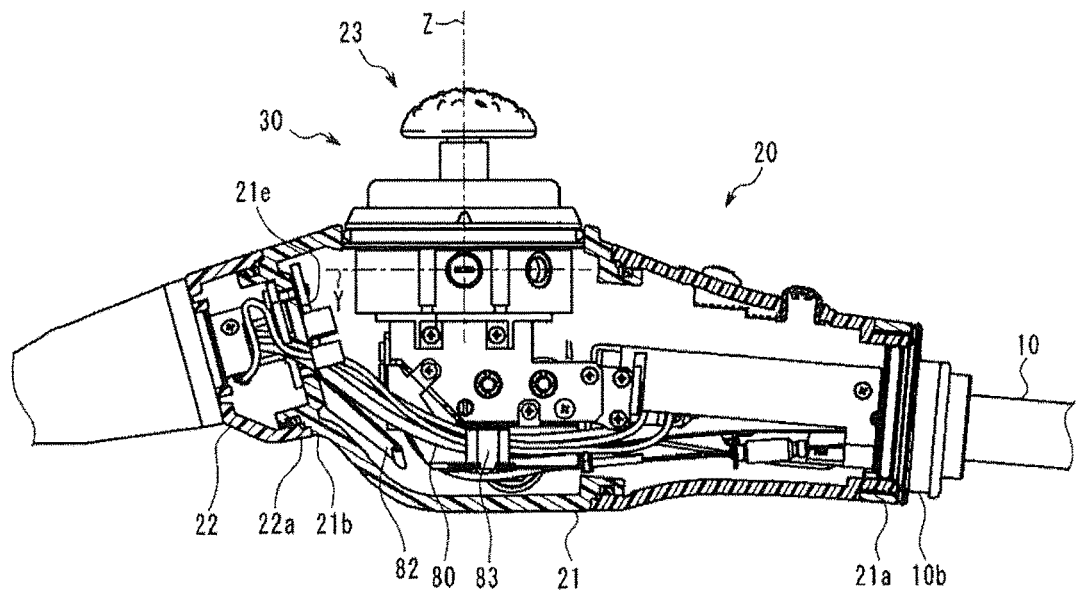
FIG. 16 is a cross-section view in which the inside of the operation portion according to the sixth embodiment is viewed from the right side.

FIGS. 15 and 16 are cross-section views in which handling of a plurality of linear internal components 80 is shown inside the operation portion 20. FIG. 15 is a diagram in which the inside of the operation portion 20 is viewed from the left side and FIG. 16 is a diagram in which the inside of the operation portion 20 is viewed from the right side.

In the present embodiment, the linear internal component 80 includes a member an outer shape of which is linear, which is inserted from the inside of the insertion portion 10 to the inside of the universal cable 90 through the inside of the operation portion 20, such as an electrical cable or an optical fiber cable connected to the image pickup apparatus 14. Also, the linear internal component 80 includes an electrical cable connected to an electronic instrument or metal frame such as a switch provided on the operation portion 20 and inserted into the inside of the operation portion 20 and the inside of the universal cable 90. Also, the linear internal component 80 may include a hollow tube in addition to an electrical cable and an optical fiber cable.

As shown in FIGS. 15 and 16, the proximal end 10b of the cylindrical insertion portion 10 is fixed on the distal end 21a of the main body portion 21 of the operation portion 20. On the other hand, the distal end 22a of the cylindrical grip 22 is fixed on the proximal end 21b of the main body portion 21.

In the endoscope 1 according to the present embodiment, the insertion portion 10 and the grip 22 fixed to the main body portion 21 are arranged so as to extend from the main body portion 21 using a direction substantially along the Y axis as the longitudinal direction. Further, in the endoscope 1 according to the present embodiment, in a case in which the operation portion 20 is viewed from a direction parallel to the X axis as shown in FIGS. 15 and 16, a connecting part between the main body portion 21 and the insertion portion 10 is placed below a connecting part between the main body portion 21 and the grip 22. In other words, the connecting part between the main body portion 21 and the grip 22 is offset above the connecting part between the main body portion 21 and the insertion portion 10.

Accordingly, the linear internal component 80 extending to the inside of the main body portion 21 from the inside of the insertion portion 10 backward is handled in a shape in which the linear internal component 80 passes through the lower side of the main body portion 21, and afterward gently bends upward once, and afterward gently bends backward along the longitudinal direction of the grip 22 in the vicinity of an entry of the grip 22. Note that handling of the linear internal component 80 in the lower side in the main body portion 21 is also to avoid an interference with the swinging mechanism 30, the pulling mechanism 40, or the like provided on the inside of the main body portion 21.

Specifically, a shape in a section from the inside of the main body portion 21 up to the inside of the universal cable 90 through the grip 22 of the linear internal component 80 may be called as a gentle crank shape or a gentle S shape.

In the endoscope 1 according to the present embodiment, an outer circumference in a section from the inside of the main body portion 21 of the linear internal component 80 up to the inside of the universal cable 90 through the grip 22 is covered by a heat shrinkable tube 81 that is a protective tube having flexibility (shown in FIG. 15).

When transporting or handling the endoscope 1, the universal cable 90 may be wound and assembled in the shape of a coil after arranging the electrical connecting portion 94 and the light source connector portion 93. Particularly, in a case in which the endoscope 1 after the cleansing and the sterilization process are performed is not caused to be contacted with a floor and a person assembles the endoscope 1, the operation portion 20 is gripped by one hand and an operation to wind the universal cable 90 by the other hand is performed. In this case, when the universal cable 90 is wound in a U-shaped slacked state, torsion is caused in the linear internal component 80 of the universal cable 90. A deformation in the torsional direction is hardly transmitted to the front side in comparison to a portion in which the linear internal component 80 is bent in the crank shape in the vicinity of the grip 22. Therefore, in a case in which a force in the torsional direction is applied to the linear internal component 80 by torsion caused in a U-shaped slacked portion of the universal cable 90, a large deformation in the torsional direction may be generated between a portion bent in the crank shape in the vicinity of the grip 22 and the U-shaped slacked portion of the universal cable 90 and the linear internal component 80 may be damaged.

In the endoscope 1 according to the present embodiment, a portion easy to generate a deformation in the torsional direction of the linear internal component 80, concretely, a portion from the U-shaped slacked portion of the universal cable 90 up to a portion bent in the crank shape inside the operation portion 20 is covered by the heat shrinkable tube 81, and thereby a strength to the deformation in the torsional direction of the linear internal component 80 is enhanced. Concretely, rigidity of a portion covered by the heat shrinkable tube 81 of the linear internal component 80 is enhanced, and therefore a kink or buckling due to the deformation in the torsional direction is suppressed from being caused. Note that, in the present embodiment, the endoscope 1 has a configuration in which flexibility is also borne while the rigidity of the linear internal component 80 is enhanced by covering the linear internal component 80 by the heat shrinkable tube 81. Further, the rigidity of a member constituting the linear internal component 80 may be enhanced.

Note that the heat shrinkable tube 81 is preferably made of a material that softens and shrinks at a temperature higher than an upper limit temperature of an autoclave sterilization process performed on the endoscope 1. By using the heat shrinkable tube 81 made of the material, when the autoclave sterilization process is performed on the endoscope 1, after the heat shrinkable tube 81 softens, it is possible to prevent the heat shrinkable tube 81 from being re-cured in a shape different from the shape at the time of manufacturing the endoscope 1 and from getting wrinkled.

Figure 17:
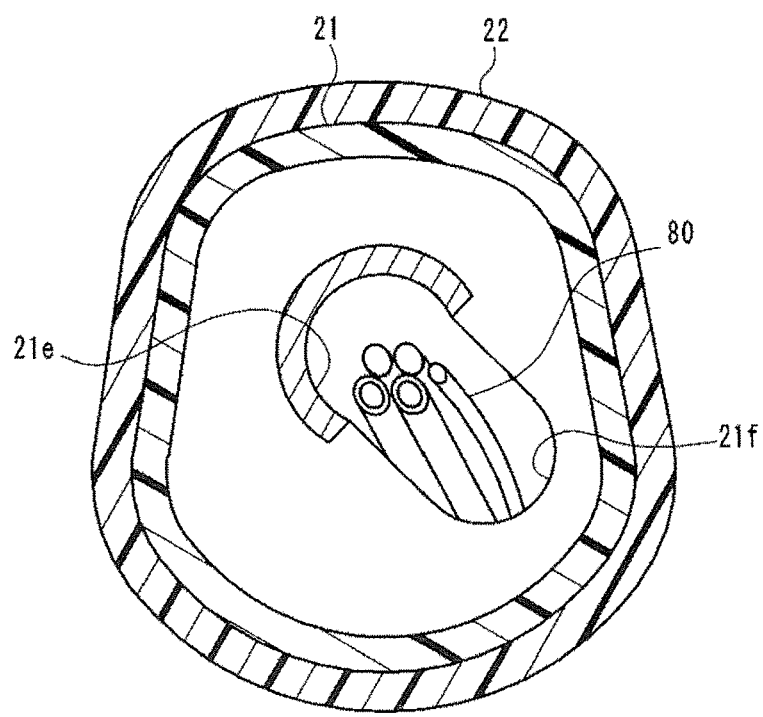
FIG. 17 is a XVII-XVII cross-section view of FIG. 15.

In FIG. 17, a XVII-XVII cross-section view of FIG. 15 is shown. As shown in FIG. 17, in the present embodiment, a cut-out part 21*f* that expands a communicating hole 21*e* in a right down direction is formed in the communicating hole 21*e* that communicates the distal end 22*a* of the grip 22 with the proximal end 21*b* of the main body portion 21.

The linear internal component 80 is handled so as to pass through the cut-out part 21*f,* and thereby a curvature radius of bending of the linear internal component 80 in a bonding part between the grip 22 and the main body portion 21 can be increased and a stress applied to the linear internal component 80 can be relaxed.

As shown in FIGS. 15 and 16, a cable guide 82 made of a tongue-shaped member provided along the linear internal component 80 is arranged in the vicinity of the communicating hole 21*e* inside the main body portion 21. By providing the cable guide 82, a work for inserting the linear internal component 80 into the inside of the communicating hole 21*e* from the inside of the main body portion 21 is facilitated when manufacturing the endoscope 1.

Further, as shown in FIG. 16, a cable duct 83 made of a cylindrical member formed by folding a metal plate in a tubular shape is arranged downside of the inside of the main body portion 21. A plurality of the linear internal components 80 are inserted into the inside of the cable duct 83. A handling position of the linear internal component 80 inside the main body portion 21 is determined by the cable duct 83.

Note that a hemming bending processing is applied to an end part of the cable duct 83 made of a metal plate and an angular part of the metal plate is prevented from coming into contact with the linear internal component 80. Thereby, a keen part of the metal plate can be prevented from coming into contact with the linear internal component 80 and the linear internal component 80 can be prevented from being damaged.

Figure 18:
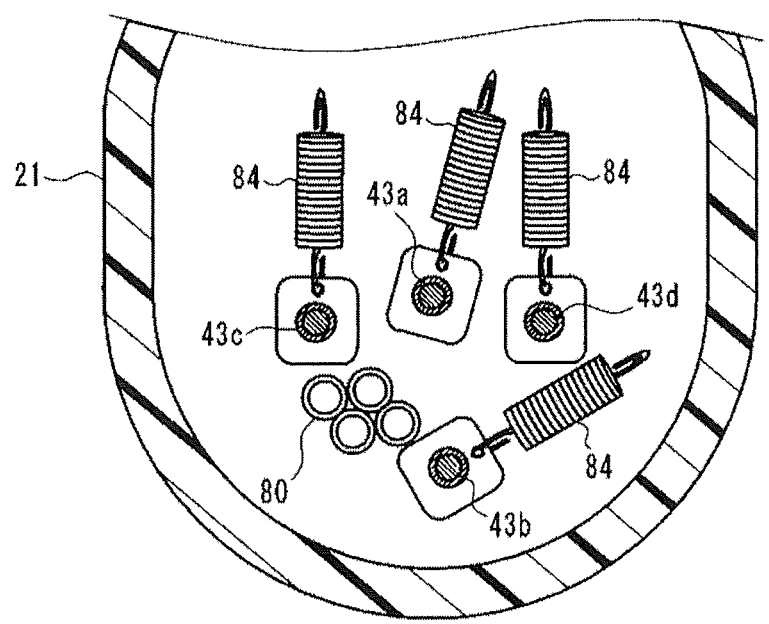
FIG. 18 is a XVIII-XVIII cross-section view of FIG. 15.

In FIG. 18, a XVIII-XVIII cross-section view of FIG. 15 is shown. A site in which the four wires 43*a* to 43*d* described above and a plurality of the linear internal components 80 are concentrated toward the inside of the insertion portion 10 is provided on the side of the distal end 21*a* inside the main body portion 21. In the endoscope 1 according to the present embodiment, as shown in FIG. 18, an energizing force is applied to the four wires 43*a* to 43*d* in a direction separated from the linear internal component 80 by four pulling coil springs 84 in the vicinity of the distal end 21*a* inside the main body portion 21. The four pulling coil springs 84 are installed between a frame member (not shown) inside the main body portion 21 and the four wires 43*a* to 43*d*, respectively.

As described above, the four wires 43*a* to 43*d* are pulled so as to be separated from the linear internal components 80 by the four pulling coil springs 84, which can prevent an interference between the four wires 43*a* to 43*d* and the linear internal components 80 in the distal end 21*a* inside the main body portion 21.

The present invention is not limited to the above-described embodiment and can be appropriately changed without departing from the spirit or idea of the invention that can be read from the claims and the entire specification. An endoscope and an operation portion accompanying such a change are also included in the technical scope of the present invention

What is claimed is:

1. An endoscope comprising:
   an insertion portion including a bending portion;
   a plurality of wires each:
   having a distal end connected to the bending portion; and
   being inserted into the insertion portion;
   an operation portion fixed in a proximal end of the insertion portion, the plurality of wires extending from an inside of the insertion portion to an inside of the operation portion;
   a swinging mechanism:
   provided on the operation portion; and
   configured to swingably support an operation stick protruding from the operation portion;
   a pulling mechanism provided on the operation portion, proximal ends of the plurality of wires being connected to the pulling mechanism, the pulling mechanism being configured to change a pulling amount of each of the plurality of wires in accordance with an inclination angle and an inclination direction from a predetermined neutral position of the operation stick;
   at least one tubular member provided on the operation portion and including a first part extending in a direction of a longitudinal axis of the insertion portion, a second part provided on a proximal end side of the first part and extending in a side direction to the longitudinal axis, and a bent part connecting the first part and the second part, at least one wire of the plurality of wires being inserted into the at least one tubular member; and
   a stopper fixed in the operation portion and arranged so as to prevent movement of the bent part by abutting on an inside of bending of the bent part;
   wherein the first part and the second part of the at least one tubular member are each fixed to the operation portion;

the stopper includes two contact parts that contact with the bent part in two points separated in a longitudinal direction of the tubular member;

where a tensile force is not applied to the at least one wire inserted into the at least one tubular member, the at least one tubular member is separated from contacting at least one of the two contact parts, and where the tensile force is applied to the at least one wire inserted into the at least one tubular member, the at least one tubular member abuts on each of the two contact parts.

2. The endoscope according to claim 1, wherein the operation stick includes an end part arranged on the inside of the operation portion, the end part is connected to an axial member arranged on the inside of the operation portion by a ball joint, and the ball joint includes an opening having an inner diameter smaller than an outer diameter of a press-fitted ball and a predetermined depth in a direction in which the ball is press-fitted, and a spherical bearing receiving the press-fitted ball via the opening and having an inner diameter larger than the outer diameter of the ball.

3. The endoscope according to claim 1, further comprising:

a universal cable that extends from the operation portion; and a linear internal component that is inserted into insides of the operation portion and the universal cable, wherein the linear internal component includes a portion bent in a crank shape inside the operation portion, and an outer circumference of a section from the portion bent in the crank shape of the linear internal component up to the universal cable is covered by a protective tube having flexibility.

4. An operation portion comprising:

a body:

at least one tubular member provided in an inside of the body, the at least one tubular member comprising:

a first part in which the at least one tubular member is fixed in the inside of the body, a second part that extends in a direction different from the first part and is fixed in the inside of the body, and a bent part being bent to connect the first part and the second part; and a stopper fixed in the inside of the body and configured to prevent movement of the bent part by abutting on an inside of bending of the bent part, wherein the stopper includes two contact parts that contact with the bent part in two points separated in a longitudinal direction of the tubular member;

where a tensile force is not applied to a wire inserted into the at least one tubular member, the at least one tubular member is separated from contacting at least one of the two contact parts, and where the tensile force is applied to the wire inserted into the at least one tubular member, the at least one tubular member abuts on each of the two contact parts.

* * * * *